US012303253B2

(12) United States Patent
Stever et al.

(10) Patent No.: US 12,303,253 B2
(45) Date of Patent: May 20, 2025

(54) SYSTEMS AND METHODS OF TRACKING PATIENT MOVEMENT

(71) Applicant: ZOLL Medical Corporation, Chelmsford, MA (US)

(72) Inventors: Timothy F. Stever, Lowell, MA (US); Bruce H. Edwards, Marlborough, MA (US); Gary A. Freeman, Waltham, MA (US); Brandon W. Marvenko, North Huntingdon, PA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 15/475,360

(22) Filed: Mar. 31, 2017

(65) Prior Publication Data
US 2017/0281054 A1 Oct. 5, 2017

Related U.S. Application Data

(60) Provisional application No. 62/316,196, filed on Mar. 31, 2016.

(51) Int. Cl.
*A61B 5/11* (2006.01)
*A61B 5/00* (2006.01)
(Continued)

(52) U.S. Cl.
CPC .......... *A61B 5/1114* (2013.01); *A61B 5/0024* (2013.01); *A61B 5/1117* (2013.01);
(Continued)

(58) Field of Classification Search
CPC .......... A61B 5/1117; A61B 2562/0219; A61B 5/1116; A61B 5/1118; A61B 5/1123; A61B 5/1114; A61B 5/746
See application file for complete search history.

(56) References Cited

U.S. PATENT DOCUMENTS 6,696,957 B2   2/2004 Shepher
7,149,579 B1   12/2006 Koh et al.
(Continued)

FOREIGN PATENT DOCUMENTS

CN    1754583 A    4/2006
CN    103002800 A  3/2013
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.
(Continued)

*Primary Examiner* — Thaddeus B Cox
*Assistant Examiner* — Karen E Toth
(74) *Attorney, Agent, or Firm* — Finch & Maloney PLLC

(57) ABSTRACT

An ambulatory medical device is provided. The ambulatory medical device includes at least one sensor configured to acquire sensor data descriptive of patient motion and at least one processor coupled to the at least one sensor. The at least one processor is configured to detect the patient motion from the sensor data, and to classify the patient motion.

21 Claims, 13 Drawing Sheets

(51) Int. Cl.
*A61B 5/113* (2006.01)
*A61B 5/33* (2021.01)
*A61B 5/349* (2021.01)
*A61B 5/361* (2021.01)
*A61B 5/364* (2021.01)
*A61N 1/39* (2006.01)
*G16H 10/60* (2018.01)
*G16H 20/00* (2018.01)
*G16H 50/20* (2018.01)

(52) U.S. Cl.
CPC ............... *A61B 5/113* (2013.01); *A61B 5/33* (2021.01); *A61B 5/349* (2021.01); *A61B 5/361* (2021.01); *A61B 5/4094* (2013.01); *A61B 5/6831* (2013.01); *A61N 1/3925* (2013.01); *G16H 10/60* (2018.01); *G16H 20/00* (2018.01); *G16H 50/20* (2018.01); *A61B 5/364* (2021.01); *A61B 2562/0219* (2013.01)

(56) References Cited

U.S. PATENT DOCUMENTS

| | | |
|---|---|---|
| 7,974,689 B2 | 7/2011 | Volpe et al. |
| 8,140,154 B2 | 3/2012 | Donnelly et al. |
| 8,676,313 B2 | 3/2014 | Volpe et al. |
| 2005/0237207 A1 | 10/2005 | Gilbert et al. |
| 2006/0241521 A1* | 10/2006 | Cohen ............... A61B 5/1112 600/595 |
| 2007/0118056 A1 | 5/2007 | Wang et al. |
| 2007/0169364 A1 | 7/2007 | Townsend et al. |
| 2008/0312709 A1 | 12/2008 | Volpe et al. |
| 2010/0010583 A1 | 1/2010 | Panken et al. |
| 2010/0076533 A1 | 3/2010 | Dar et al. |
| 2010/0179451 A1* | 7/2010 | Hately ............... G16H 40/67 600/595 |
| 2010/0298650 A1 | 11/2010 | Moon et al. |
| 2010/0298653 A1* | 11/2010 | McCombie .......... A61B 5/0002 600/301 |
| 2010/0298659 A1 | 11/2010 | McCombie et al. |
| 2010/0298899 A1* | 11/2010 | Donnelly ............ A61B 5/02055 607/6 |
| 2010/0312297 A1 | 12/2010 | Volpe et al. |
| 2011/0245629 A1 | 10/2011 | Giftakis et al. |
| 2014/0163425 A1* | 6/2014 | Tran ................... A61B 5/02055 600/595 |
| 2014/0171749 A1* | 6/2014 | Chin .................... A61B 5/0015 600/300 |
| 2014/0303680 A1 | 10/2014 | Donnelly et al. |
| 2015/0018014 A1* | 1/2015 | Phan ....................... G01P 13/00 455/456.3 |
| 2015/0120336 A1* | 4/2015 | Grokop .................. H04R 3/002 705/4 |
| 2015/0157242 A1 | 6/2015 | Sabesan |
| 2015/0223541 A1 | 8/2015 | Miller, II |
| 2016/0074667 A1 | 3/2016 | Sullivan et al. |
| 2016/0278652 A1 | 9/2016 | Kaib et al. |

FOREIGN PATENT DOCUMENTS

| | | |
|---|---|---|
| CN | 104168825 A | 11/2014 |
| CN | 104736055 A | 6/2015 |
| JP | 2001327482 A | 11/2001 |
| JP | 2002200059 A | 7/2002 |
| JP | 2009039466 A | 2/2009 |
| JP | 2009-195598 A | 9/2009 |
| JP | 2010213782 A | 9/2010 |
| JP | 2013530776 A | 8/2013 |
| JP | 2016-504663 A | 2/2016 |
| WO | 2012006524 A1 | 1/2012 |
| WO | 2016106132 A2 | 6/2016 |

OTHER PUBLICATIONS

O'Keeffe et al., "Reproducability and responsiveness of quality of life assessment and six minute walk test in elderly heart failure patients," Heart (1998) 80: 377-382.
PCT Search Report and Written Opinion for PCT Application No. PCT/US2017/025271, mailed on Jun. 16, 2017, 16 pages.
Li Deng et al., "Deep Learning Methods and Applications", Foundations and Trends in Signal Processing, 2013, pp. 197-387, vol. 7, Issues 3-4.
Skog et al., "Zero-Velocity Detection—Algorithm Evaluation", IEEE Trans. Biomed. Eng., Nov. 2010, pp. 2657-2666, vol. 57, No. 11.
Philips Lifeline, "Discover Why More People Choose Philips Lifeline Than Any Other Medical Device", Brochure, 2017, 2 pages.
Extended European Search Report for European Application No. 17776740.7, mailed on Aug. 19, 2019, 8 pages.
Chinese Notification of the First Office Action for Application No. 201780021859.2 dated Dec. 3, 2020, 10 pages.
Japanese Office Action for Application No. 2018-544566 dated Jan. 26, 2021, 8 pages.
Decision of Dismissal of Amendment, Japan Patent Application 2018-544566 (Jun. 1, 2022) (includes machine-generated English translation).
Japan Patent Application 2018-544566, Reconsideration Report by Examiner Before Appeal, sent Nov. 15, 2022.
China Patent Application 2017-80021859.2, Office Action dated Jul. 21, 2022.
Europe Patent Application 17776740.7, Examination Report dated Aug. 4, 2022.
Japan Patent Application 2018-544566, Office Action dated Sep. 14, 2021.

* cited by examiner

SYSTEMS AND METHODS OF TRACKING PATIENT MOVEMENT

RELATED APPLICATIONS

This application claims priority under 35 U.S.C. § 119(e) to U.S. Provisional Application Ser. No. 62/316,196 filed Mar. 31, 2016. All subject matter set forth in the above referenced application is hereby incorporated by reference in its entirety into the present application as if fully set forth herein.

BACKGROUND

This disclosure relates to systems and methods of tracking patient movement.

Health care outcomes in clinical settings can be improved by prompt detection of events indicating some change in the wellbeing of a patient. Clinical settings, such as in-patient hospital areas, monitor various vital signs (e.g., blood pressure, pulse, respiration rate) of a patient to detect changes. The monitored vital signs are often transmitted to a central station where health care providers evaluate the vital signs and respond to any changes that warrant further investigation.

SUMMARY

Some ambulatory medical devices include components capable of tracking patient movement. These components may include, for example, one or more inertial measurement units (IMUs), such as accelerometers, gyroscopes, and magnetometers. In a hospital setting, detailed, continuous, real time tracking of patient movement and patient orientation by an ambulatory medical device can improve patient care by addressing a variety of situations not addressable via conventional techniques. In various implementations described in this disclosure, motion parameters include orientation parameters. Accordingly, unless expressly noted, references to motion of a patient's body or a portion of a patient's body includes orientation in space of the patient's body or the portion of the patient's body.

Thus, and in accordance with some examples of the present disclosure, a medical device including an IMU is provided. The medical device is configured to monitor a patient for particular types of motion and to respond to detection of some types of motion by taking an action associated with the motion type and designed to prevent or address consequences of the type of patient motion. Types of patient motion that some examples are configured to detect and address include seizures, shivering, coughing, disoriented movement, movement associated with regaining of consciousness, sleepwalking, falling, stumbling, and swooning. In some examples, the medical device is configured to detect these and other types of patient motion based on a baselining or training (i.e. a patient-specific motion recognition training) period whereby the motion/orientation sensors are affixed to the appropriate portions of the patient's body and the patient is instructed to make a series of predefined movements or activities. For example, such baselining and/or training may be recorded during an initial fitting of the medical device to the patient, and the data can be improved over time as the device learns the patient's motion behavior during use. Alternatively or additionally, medical devices in accord with some examples detect types of patient motion without reference to specific baseline or training information but instead with reference to more common, yet distinctive, characteristics of types of patient motion, such as magnitudes of forces on the patient brought about by patient motion and/or frequency of the patient motion.

In at least one example, an ambulatory medical device for monitoring patient movement is provided. The ambulatory medical device includes a plurality of motion sensors configured to be located at one or more anatomical locations on a patient's body and to detect a plurality of motion parameters corresponding to a motion of a portion of the patient's body; and at least one processor communicatively coupled to the plurality of motion sensors, the at least one processor configured to receive the plurality of motion parameters corresponding to the motion of the portion of the patient's body; store, in a data store, the plurality of motion parameters; process the plurality of motion parameters stored in the data store to determine the motion of the portion of the patient's body; classify the motion of the portion of the patient's body based on a plurality of predetermined motion sentence features, the plurality of predetermined motion sentence features comprising at least one predetermined motion primitive, and initiate one or more notification actions based on the classification.

In the ambulatory medical device, the plurality of motion parameters may include at least one orientation parameter corresponding to an orientation of the portion of the patient's body. The plurality of motion sensors may include at least one of an accelerometer, a gyroscope, and magnetometer. The plurality of predetermined motion sentence features may include a plurality of predetermined motion primitives, at least one predetermined motion modifier, at least one predetermined motion object, at least one predetermined motion sentence, and at least one predetermined sequence of motion sentences. The at least one processor may be configured to classify the motion of the patient with reference to first sensor data acquired from a first motion sensor attached to a first location and second sensor data acquired from a second motion sensor attached to a second location. The one or more anatomical locations on the patient's body may include one or more of a head, chest, leg, neck, shoulder, elbow, knee, wrist, jaw, forearm, bicep, ankle, and foot of the patient's body. The first location may include an anatomical location on the patient and the second location may include a location of a physical object other than the patient. The physical object may include at least one of a bed and a wheelchair. The at least one processor may be configured to classify the motion based on one or more motion detection rules derived from a database of pre-collected motion information.

In the ambulatory medical device, the at least one processor may be configured to classify the motion using on a motion recognition process and train the motion recognition process using at least one of predetermined measured motions from multiple patients and patient-specific motion derived during a baselining period. The patient-specific motion derived during the baselining period may be recorded during at least one of a sleep period and a six-minute walk test period. The one or more notification actions may include notifying a caregiver about the motion of the patient. The one or more notification actions may include warning the patient based on the motion of the patient. The at least one processor may be configured to identify another medical device separate from the ambulatory medical device proximal to the patient and to instruct the medical device to issue an alert. The at least one processor may be configured to identify the current time and to execute an action associated with the current time. The at least one processor may be configured to classify the motion of the patient as at least one of disoriented movement, falling, stumbling, swooning, seizure, shivering, and coughing. The ambulatory medical device may further comprise a wearable defibrillator. The ambulatory medical device may further comprise a mobile cardiac monitoring device.

In another example, a system for monitoring patient movement is provided. The system includes a cardiac monitoring device. The cardiac monitoring device includes a plurality of motion sensors configured to be located at one or more anatomical locations on a patient's body to detect a plurality of motion parameters corresponding to a motion of a portion of the patient's body and at least one processor communicatively coupled to the plurality of motion sensors. The at least one processor is configured to transmit the plurality of motion parameters corresponding to the motion of the portion of the patient's body to a remote server. The remote server is configured to receive the plurality of motion parameters corresponding to the motion of the portion of the patient's body; store, in a data store, the plurality of motion parameters; process the plurality of motion parameters stored in the data store to determine the motion of the portion of the patient's body; classify the motion of the portion of the patient's body based on a plurality of predetermined motion sentence features, the plurality of predetermined motion sentence features comprising at least one predetermined motion primitive; and initiate one or more notification actions based on the classification. The system may further include at least one client device in communication with the remote server, the at least one client device being configured to notify at least one of a caregiver and the patient about the motion of the patient based on the one or more notification actions.

In one example, an ambulatory medical device is provided. The ambulatory medical device includes at least one sensor configured to acquire sensor data descriptive of patient motion and at least one processor coupled to the at least one sensor. The at least one processor is configured to detect the patient motion from the sensor data, to classify the patient motion using, e.g., template matching, known to those skilled in the art, wherein measured and detected motion features are compared to templates derived from a pre-collected database of measured motions from multiple patients or other users, or from a patient-specific templates derived during the patient-specific baselining or training period, and to execute a notification component associated with the at least one predetermined templates.

In the ambulatory medical device, the at least one sensor may include at least one of an accelerometer, a gyroscope, and magnetometer. The at least one processor may be configured to classify the patient motion as at least one motion sequence including at least one motion primitive. The at least one sensor may include a plurality of sensors. The at least one processor may be configured to classify the patient motion with reference to first sensor data acquired from a first sensor attached to a first location and second sensor data acquired from a second sensor attached to a second location. The first location and the second location may be anatomical locations on the patient. The first location and the second location may be separated by a joint of the patient. The joint may be at least one of a knee and an elbow of the patient. The first location may be an anatomical location on the patient and the second location may be a location of a physical object other than the patient. The physical object may include at least one of a bed and a wheelchair. The baselining and/or training information (see, e.g., FIG. 5 below) may be recorded during at least one of sleep and a six-minute walk test. The sensor data descriptive of patient motion (including orientation) may indicate no motion.

In the ambulatory medical device, the notification component may be configured to notify a caregiver of the patient motion. The notification component may be configured to warn the patient. The at least one processor may be configured to identify a medical device associated with a condition of the patient and proximal to the patient and to instruct the medical device to issue an alert. The condition may be associated with the patient motion. The at least one processor may be configured to execute an action associated with an age of the patient. The at least one processor may be configured to identify the current time and to execute an action associated with the current time. The ambulatory medical device may be configurable between a day mode and a night mode and the at least one processor may be configured to identify a current mode as either the day mode or the night mode and to execute an action associated with the current mode. The at least one processor may be further configured to prompt the patient to perform a series of motions, and record a template of the patient performing each motion in the series.

In another example, an ambulatory medical device is provided. The ambulatory medical device includes at least one inertial measurement unit and at least one processor coupled to the at least one inertial measurement unit. The ambulatory medical device is configured to detect a patient fall at least in part by identifying a sequence of measurements, the sequence including a first acceleration less than a first threshold, a second acceleration greater than a second threshold, and a third acceleration within a range of thresholds.

In the ambulatory medical device, the first threshold may equal 0.5 $g_o$, the second threshold may equal 8 $g_o$, and the range of thresholds equals [0.95 $g_o$, 1.05 $g_o$]. The at least one processor may be configured to calculate a confidence metric and to detect the patient fall where the confidence metric exceeds a fourth threshold. The at least one processor may be configured to act upon detecting the patient fall, the act including at least one of prompting the patient to confirm the fall, notifying bystanders of the fall, and notifying hospital personnel of the fall.

In another example, a hospital-based ambulatory defibrillator is provided. The hospital-based ambulatory defibrillator includes at least one adhesive electrode configured to acquire data descriptive of a patient, at least one inertial measurement unit, and at least one processor coupled to the at least one adhesive electrode and the at least one inertial measurement unit. The at least one processor is configured to monitor patient movement via the at least one inertial measurement unit.

In the hospital-based ambulatory defibrillator, wherein the at least one processor may be configured to classify the patient movement as at least one of disoriented movement, falling, stumbling, and swooning. In an implementation, the at least one processor may be configured to classify the patient movement at least in part by comparing the patient movement to templates derived from a pre-collected database of measured motions from multiple patients or other users, or from a patient-specific templates derived during the patient-specific baselining or training period. For example, the patient-specific templates may be recorded during a six-minute walk test. The at least one processor may be configured to classify the patient movement as at least one of seizure, shivering, and coughing. The at least one processor may be configured to classify the patient movement at least in part by comparing a magnitude of the patient movement to a first threshold and a frequency of the patient movement to a second threshold. The at least one processor may be configured to classify the patient movement as at least one movement type selected from a group including disoriented movement, falling, stumbling, swooning, seizure, shivering, and coughing and to execute at least one action in response to classifying the patient movement. The at least one action may include at least one of prompting the patient to confirm that the patient movement is of the at least one movement type, notifying bystanders of the patient movement, and notifying hospital personnel of the patient movement. The at least one processor may be configured to calculate a distance of the patient from a hospital bed; and execute at least one action in response to the distance transgressing a threshold, the at least one action including at least one of prompting the patient to respond, notifying bystanders of patient movement, and notifying hospital personnel of patient movement.

In another example, a system of medical devices is provided. The system includes a hospital-based ambulatory defibrillator and a hospital bed. The hospital-based ambulatory defibrillator includes at least one adhesive electrode, at least one inertial measurement unit, and at least one processor coupled to the at least one adhesive electrode and the at least one inertial measurement unit. The at least one processor is configured to monitor patient movement via the at least one inertial measurement unit. The hospital bed may include one or more inertial measurement units and one or more processors coupled to the one or more inertial measurement units. The one or more processors are configured to monitor patient movement via the one or more inertial measurement units.

In the system of medical devices, the hospital-based ambulatory defibrillator may further include a first network interface. The hospital bed may include a second network interface configured to communicate with the first network interface. The one or more processors may be configured to transmit patient movement data to the at least one processor. The at least one processor may be configured to detect the patient leaving the hospital bed at least in part by processing the patient movement data.

In another example, a hospital-based ambulatory defibrillator is provided. The hospital-based ambulatory defibrillator includes at least one adhesive electrode configured to acquire data descriptive of a patient, at least one inertial measurement unit, and at least one processor coupled to the at least one adhesive electrode and the at least one inertial measurement unit. The at least one processor is configured to monitor patient movement during sleep via the at least one inertial measurement unit.

In the hospital-based ambulatory defibrillator, the at least one processor may be configured to classify the patient movement as either excessive or not excessive. The at least one processor may be configured to classify the patient movement at least in part by comparing the patient movement to templates derived from a pre-collected database of measured motions from multiple patients or other users, or from a patient-specific templates derived during the patient-specific baselining or training period. For example, the patient-specific templates may be recorded during normal patient sleep. The at least one processor may be configured to classify the patient movement at least in part by comparing a magnitude of the patient movement to a first threshold and a frequency of the patient movement to a second threshold.

In the hospital-based ambulatory defibrillator, the data descriptive of the patient may include electrocardiogram data. The at least one inertial measurement unit may be configured to acquire heart sounds of the patient. The at least one processor may be configured to analyze the patient movement and at least one of the electrocardiogram data and the heart sounds to determine a condition of the patient.

The hospital-based ambulatory defibrillator may further include a network interface coupled to the at least one processor. The data descriptive of the patient may include electrocardiogram data. The at least one processor may be configured to transmit the patient movement and the electrocardiogram data to a distinct medical monitoring device.

In the hospital-based ambulatory defibrillator, the at least one processor may be configured to alter an arrhythmia treatment protocol in response to classifying the patient movement as excessive. The at least one processor may be configured to alter the arrhythmia treatment protocol by prepending a tactile alert and an alert to hospital personnel to a default arrhythmia treatment protocol.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
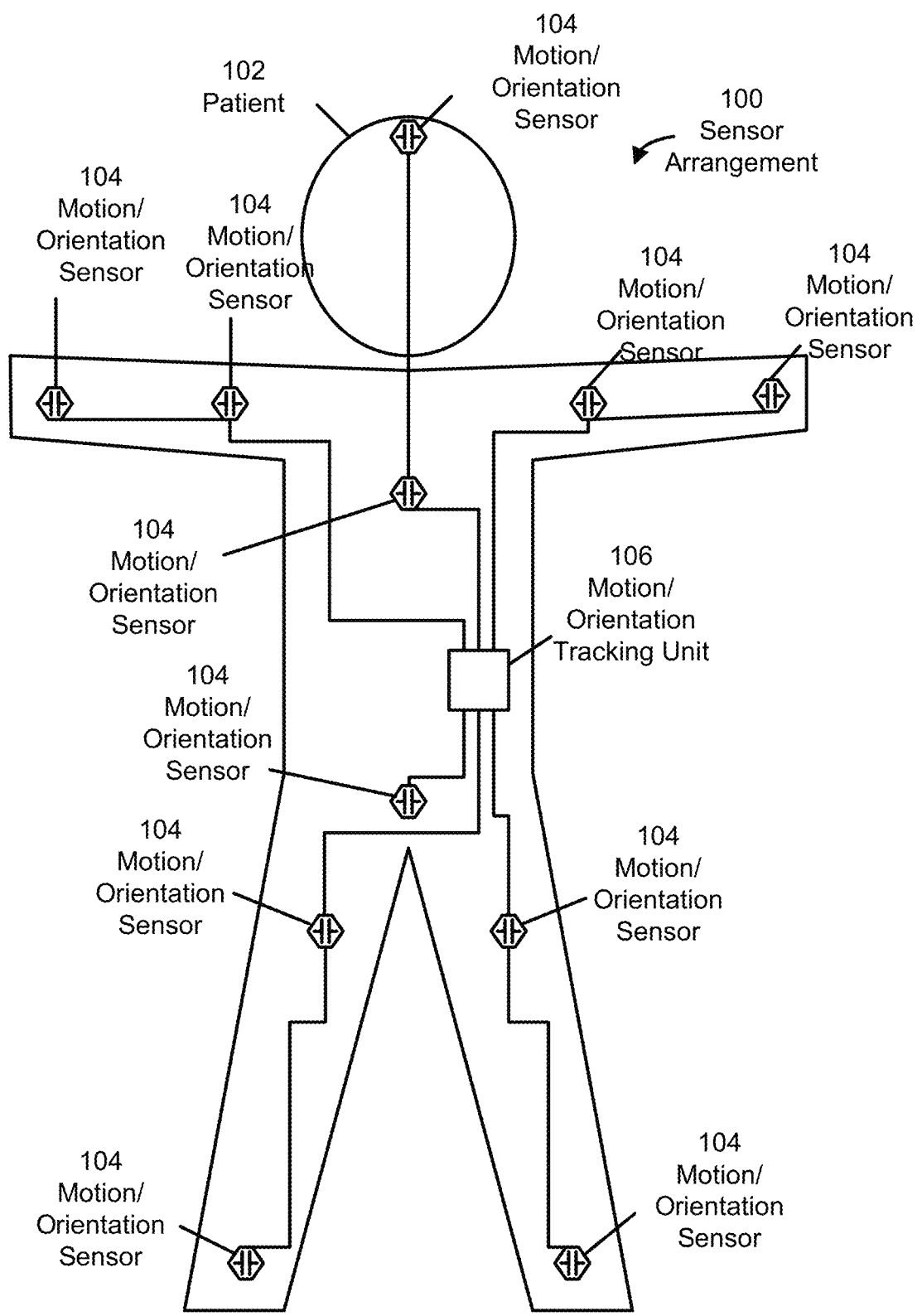
FIG. 1 is a schematic illustration of a sensor arrangement that includes a plurality of motion/orientation sensors disposed proximate to a patient and that are in communication with a motion tracking unit in accordance with an example of the present disclosure.

Examples described herein include an ambulatory medical device having at least one sensor used to acquire motion parameters comprising data descriptive of patient motion. As described in further detail below, in various implementations the motion parameters include patient orientation parameters. Accordingly, in this disclosure references to motion of a patient's body or a portion of a patient's body include orientation in space of the patient's body or the portion of the patient's body. The sensor(s) can be attached to clothing worn by a patient or attached to the patient himself by some releasable coupling, such as by a band or a temporary adhesive compatible with human skin or clothing. Regardless of to which portion(s) of the patient the sensor(s) are attached (e.g., head, arm(s), leg(s), thorax), motion (including orientation) of that portion of the patient is measured. The ambulatory medical devices use the acquired data to detect, and in some instances classify, the patient motion. Data corresponding to the measured motion is collected and processed to estimate the motion (including orientation in space) at that particular sensor location. The motion or orientation measurements are processed to detect a sequence of one or more predetermined motion or orientation types (a "motion primitive"), and to classify the motion primitives based on features of the motion waveforms as corresponding to one or more predetermined motion primitives. Some examples of motion primitives might be: "lying", "sitting", "standing", "placing foot", "falling", "rolling", "walking", "running", "turning", "bending", "straightening".

Additionally, there may be motion modifiers to the motion primitives such as "fast" or "slow" describing the speed of the motion, or, for example, "up", "down", "left", "right" describing directionality. Additionally, there may be motion objects, for example, "leg" or "arm" or "torso" for the body location where the sensor is located. Additionally there may be motion object modifiers (i.e. motion adjectives), for example, "left" or "right" describing which arm or leg is moving, or "upper" or "lower" describing which portion of the torso, arm, leg or other body part is moving. In some cases there may be an associated set of predefined rules for allowable detected sequence of motion primitives or motion modifiers, the predefined rules constituting a motion grammar. Using the detected motion primitives and motion modifiers, and based on a motion grammar, motion sentences can be constructed, for instance, "taking a step", "sitting up in bed", "opening a door", "walking quickly down the hall", or "falling to the ground".

This motion recognition process of detection of motion primitives, modifiers, objects, adjectives, and grammatical structure may be accomplished with a "baselining" or training (i.e. a patient-specific motion recognition training) period whereby the motion/orientation sensors are affixed to the appropriate portions of the patient's body and the patient is instructed to make a series of predefined movements or activities, for instance, lying down, sitting, getting up from sitting, getting up from lying down, walking, etc. The system then analyzes the patient's specific motions or activities and uses it to increase the accuracy of the recognition of that patient's motion. Alternatively, the motion recognition process may not employ any baselining or training period, and may rely entirely on motion detection rules derived entirely from a database of motions collected prior to the rule generation.

The outputs of the motion recognition (MR) process (e.g. motion primitive, modifiers, objects, adjectives, and grammatical structure) may then be analyzed to determine whether the MR outputs pose a threat to the health or safety of the patient, or otherwise constitute an incipient hazard. A notification component (such as an alarm or notification to a health care provider or other caregiver) may then be executed in response to the classification of the detected motion.

The estimated motion (including orientation in space) at that particular sensor location may be a vector of motion-related parameters, for instance, acceleration, velocity, position, and rotation along one or more axes (e.g. x, y, z axes). The motion vector may also include other information relevant to the motion recognition process such as time-of-day, location (e.g. geographical location learned via a GPS system, or in-building location such as bedroom, stairs, hallway, outside), or weather. In some embodiments, the axes of the accelerometer or other type of motion or orientation sensor may be positioned on or near the sternum and are aligned with the principal axes of the body, e.g. the longitudinal (vertical: e.g. "z" axis of accelerometer sensor), the transverse (horizontal: e.g. "x" axis of accelerometer sensor), or sagittal axes.

In some embodiments, the motion recognition may be based on a Hidden Markov Model (HMM) with the sequence of motion parameter vectors as the input. A state transition matrix can be developed using HMM techniques known to those skilled in the art. In particular, the sequence of motion parameter estimates, motion primitives, and motion sentences is modeled as a hidden Markov model (HMM), defined as a variant of a finite state machine having a set of states, Q, an output alphabet, O, transition probabilities, A, output probabilities, B, and initial state probabilities, Π. The current state is not observable. Instead, each state produces an output with a certain probability (B). Usually the states, Q, and outputs, O, are understood, so an HMM is said to be a triple, $\lambda=(A, B, \Pi)$. Each value of output alphabet, O, can be given a unique threshold and coefficient set. For instance, the HMM will have the transition probabilities stored in it, as a result either of database or patient-specific training, indicating such understood "facts" (i.e. motion grammar). For instance, that it is a very low probability that a person will "Sit Up" directly after having been "Standing": there must been either an intervening motion primitive that may be lost in noise, or, alternatively, since both "Sitting up" and "Falling over", "Bending Over", or "Collapsing" all may involve a rotation forward of the patient's thorax, that the probabilities of a transition to either "Falling over", "Bending", or "Collapsing" will be higher than that to "Sitting Up".

In another embodiment, if a grammatical structure of motion sentences of "Standing" followed by detection of a bending of the patient's thorax, followed by a return to "Standing" orientation two or more times (e.g. "Standing". "Bending Over". "Standing". Bending Over"), the grammatical sentence structure is detected to mean that the patient is at elevated risk of losing their balance and falling and injuring themselves, and MR outputs pose a threat to the health or safety of the patient, or otherwise constitute an incipient hazard. A notification component (such as an alarm or notification to a health care provider or other caregiver) may then be executed in response to the classification of the detected motion.

During algorithm development, the HMM is trained against a database of multiple motion types (e.g. sitting, standing walking, lying down) by multiple patients or other test subjects. In some embodiments, a patient-specific baselining or training period is provided to improve results over a basic approach lacking a patient-specific training period. For instance, the training period may be used for such refinements as: normalizing the motion parameters to patient size, e.g. torso or limb length; training to specific movement sequences by the particular patient, for instance sitting up in bed, rolling in bed, getting in and out of bed, going up stairs, walking; performing movement types in different contexts to develop context dependency (for instance, the same tests done in different rooms or different beds or different times of day); patient dependent intensity training (for instance where a patient performs the same action with differing levels of intensity).

Other techniques known in the field of HMM classification may be employed. For instance, discriminative training techniques that dispense with a purely statistical approach to HMM parameter estimation and instead optimize some classification-related measure of the training data. Examples are maximum mutual information (MMI), minimum classification error (MCE) and minimum phone error (MPE). Also, use of the Viterbi algorithm to find the best path. Other techniques are to keep a set of good candidates instead of just keeping the best candidate, and to use a better scoring function (re scoring) to rate these good candidates. The set of candidates can be kept either as a list (the N-best list approach) or as a subset of the models (a lattice). Re-scoring may be done to minimize the Bayesian risk.

In some embodiments, techniques such as dynamic time warping may be employed to minimize the impact to recognition accuracy due to motion speed. For instance, similarities in walking patterns would be detected, even if, for instance the patient was moving their legs more slowly than in the training session. Sequences are "warped" non-linearly to match each other. This sequence alignment method is often used in the context of HMMs.

In some embodiments, so-called Deep Learning Networks may be employed for motion recognition. As described in Deng, Li; Yu, Dong (2014). "Deep Learning: Methods and Applications". Foundations and Trends in Signal Processing. 7 (3-4): 197-387, deep learning networks may be classified as three major classes:

"1. Deep networks for unsupervised or generative learning, which are intended to capture high-order correlation of the observed or visible data for pattern analysis or synthesis purposes when no information about target class labels is available. Unsupervised feature or representation learning in the literature refers to this category of the deep networks. When used in the generative mode, may also be intended to characterize joint statistical distributions of the visible data and their associated classes when available and being treated as part of the visible data. In the latter case, the use of Bayes rule can turn this type of generative networks into a discriminative one for learning.

2. Deep networks for supervised learning, which are intended to directly provide discriminative power for pattern classification purposes, often by characterizing the posterior distributions of classes conditioned on the visible data. Target label data are always available in direct or indirect forms for such supervised learning. They are also called discriminative deep networks.

3. Hybrid deep networks, where the goal is discrimination which is assisted, often in a significant way, with the outcomes of generative or unsupervised deep networks. This can be accomplished by better optimization or/and regularization of the deep networks in category (2). The goal can also be accomplished when discriminative criteria for supervised learning are used to estimate the parameters in any of the deep generative or unsupervised deep networks in category (1) above."

Other common classifications are Deep Neural Networks (DNN) and Recurrent Neural Networks (RNN), Convolutional Neural Networks (CNN), Restricted Boltzman Machine (RBM), Deep Belief Network (DBN), Deep Boltzman Machine (DBM), etc.

In some embodiments, simpler MR techniques may be employed such as template matching, known to those skilled in the art, the measured and detected motion features compared to templates derived from a pre-collected database of measured motions from multiple patients or other users, or from a patient-specific templates derived during the patient-specific baselining or training period.

Example Sensor Arrangement

FIG. 1 is a schematic illustration of a sensor arrangement 100 configured to sense patient orientation and motion at the particular sensor location on the patient's body. Data corresponding to the measured motion or orientation is collected and processed to estimate the motion or orientation at that particular sensor location. The motion or orientation measurements are processed to detect a sequence of one or more predetermined motion or orientation types (a "motion primitive"), and to classify the motion primitives based on features of the motion waveforms as corresponding to one or more predetermined motion primitives. Some examples of motion primitives might be: "lying", "sitting", "standing", "placing foot", "falling", "rolling", "walking", "running", "turning", "bending", "straightening".

Additionally, there may be motion modifiers to the motion primitives such as "fast" or "slow" describing the speed of the motion, or, for example, "up", "down", "left", "right" describing directionality. Additionally, there may be motion objects, for example, for example, "leg" or "arm" or "torso" for the body location where the sensor is located. Additionally there may be motion object modifiers (i.e. motion adjectives), for example, "left" or "right" describing which arm or leg is moving, or "upper" or "lower" describing which portion of the torso, arm, leg or other body part is moving. In some cases there may be an associated set of predefined rules for allowable detected sequence of motion primitives or motion modifiers, the predefined rules constituting a motion grammar. Using the detected motion primitives and motion modifiers, and based on a motion grammar, motion sentences can be constructed, for instance, "taking a step", "sitting up in bed", "opening a door", "walking quickly down the hall", or "falling to the ground".

This motion recognition process of detection of motion primitives, modifiers, objects, adjectives, and grammatical structure may be accomplished with a "baselining" (i.e. motion recognition training) period whereby the motion/orientation sensors are affixed to the appropriate portions of the patient's body and the patient is instructed to make a series of predefined movements or activities, for instance, lying down, sitting, getting up from sitting, getting up from lying down, walking, etc. The system then analyzes the patient's specific motions or activities and uses it to increase the accuracy of the recognition of that patient's motion. Alternatively, the motion recognition process may not employ any baselining or training period, and may rely entirely on motion detection rules derived entirely from a database of motions collected prior to the rule generation.

The outputs of the motion recognition (MR) process (e.g. motion primitive, modifiers, objects, adjectives, and grammatical structure) may then be analyzed to determine whether the MR outputs pose a threat to the health or safety of the patient, or otherwise constitute an incipient hazard. A notification component (such as an alarm or notification to a health care provider or other caregiver) may then be executed in response to the classification of the detected motion.

The example sensor arrangement 100 shown includes a plurality of motion/orientation sensors 104 and a motion tracking unit 106, all of which are attached to or worn by the patient 102. The motion/orientation sensors 104 of the sensor arrangement 100 can include one or more inertial motion unit sensors ("IMU") including, but not limited to, one or more of one-dimensional accelerometers, two-dimensional accelerometers, three-dimensional accelerometers, gyroscopes, and magnetometers. For instance, examples of motion/orientation sensors 104 include multi-axis accelerometers and multi-axis gyroscopes, such as the ADIS16362iSensor® inertial system from ANALOG DEVICES®, or the iNEMO® M1 motion sensing system manufactured by STMicroelectronics® (which also includes a multi-axis magnetometer). Another example motion/orientation sensor 104 includes the MMA7361LC±1.5 g, ±6 g Three Axis Low-g Micromachined Accelerometer from Freescale Semiconductor.

Computations of the data collected by the motion/orientation sensor 104 are performed by a microprocessor disposed within the motion/orientation sensor 104 itself, or a microprocessor in communication with the motion/orientation sensor 104 and disposed elsewhere. Using data collected by the motion/orientation sensor 104 (e.g., linear acceleration, force, orientation), the microprocessor determines the location and orientation of the motion/orientation sensor 104 in three-dimensional space.

Generally, one or more IMUs can measure a change in position of the portion of the patient's body in at least three axes: pitch (up/down relative to a transverse plane), yaw (left/right relative to a sagittal plane) and roll (clockwise/counter-clockwise relative to the frontal plane, e.g., in a posterior direction or an anterior direction). Each of the measurements in these axes results in the one or more IMUs generating a series of motion parameters corresponding to the portion of the patient's body to which the one or more IMUs is attached. For example, for each of six degrees of freedom (such as x, y, z and θx, θy and θz), an IMU can integrate over time a sensed acceleration, together with an estimate of gravity, to calculate a current velocity. Then the IMU can integrate the velocity to calculate a current position. Based on the position information, the IMU can derive one or more orientation parameters for the portion of the patient's body to use in the motion recognition/classification process.

Depending on the type of sensor used for the motion/orientation sensors 104, motion, including orientation in one or more dimensions of three-dimensional space (i.e., in x, y, and z directions of a Cartesian coordinate system) is detected. Data corresponding to the motion (whether acceleration data, orientation data, or other measurement data) is detected by the motion/orientation sensors 104 and provided to the motion tracking unit 106. The data can also indicate no motion (i.e., that the patient is not moving). Furthermore, an identifier (ID) corresponding to each sensor providing data is sent to the motion tracking unit, as is a time of detection. These data are then used to classify the motion as will be discussed in more detail below in the context of FIGS. 4-6.

In the example sensor arrangement 100 shown, the motion/orientation sensors 104 are connected to one another serially along separate paths terminating at extremities of the patient 102. As shown, these various example connection paths originate at the motion tracking unit 106. One path connects several sensors along a first path terminating at a right arm of the patient 102. Another path connects several sensors along a second path terminating at a crown of the skull of the patient 102. Other analogous paths extend to the left arm of the patient 102, and the right and left legs of the patient 102. Other paths may connect one or more sensors disposed at other portions of the body of the patient 102 to the motion tracking unit 106, as needed. Additionally, some examples may omit some of the sensors 104.

The locations of the individual motion/orientation sensors 104 on the body of the patient 102 are selected with the intention of detecting motion of a portion of the patient 102 to which a corresponding motion/orientation sensor 104 is attached. In the example shown, the motion/orientation sensors 104 are attached to anatomical portions of a patient's body or generally located at anatomical locations on the patient 102, optionally separated by a joint (e.g., elbow, knee, wrist, neck, jaw) so as to detect motion of a particular segment of an arm, leg, the head, or different parts of the torso. The anatomical locations as described herein can include any location on the patient's body at which one or more motion sensors can be placed to monitor a movement, including orientation, of the underlying portion of the patient's body. For example, such anatomical locations can include one or more of a head, chest, leg, neck, shoulder, elbow, knee, wrist, jaw, forearm, bicep, ankle, and foot of the patient's body.

Configuring the motion/orientation sensors 104 in this way is beneficial for detecting motion of the patient as a whole but also for detecting motion of all body portions of the patient 102, and even one portion of the patient 102 relative to other portions of the patient 102. The motion/orientation sensor 104 can also be configured to transmit data indicating a lack of motion of portions of the patient 102. By way of illustration, motion/orientation sensors 104 attached to a torso (or worn at the torso) may be helpful in determining that the patient 102 has fallen to the ground. In another illustration, motion/orientation sensors attached to one or more legs may be helpful in determining that the patient 102 is walking. Other similar illustrations will be apparent in light of the preceding illustrations and the present disclosure.

In other examples, one or more sensors 104 of the sensor arrangement are attached to a stationary object, such as a bed or a chair (or even a wheelchair which exhibits uniform linear movement that can be distinguished from patient movement), so that patient motion is detected relative to the known stationary object. For example, if the patient 102 wearing at least one motion/orientation sensor 104 gets out of a bed to which another motion/orientation sensor 104 is attached, this relative motion between the two sensors will be detected. This can be particularly beneficial for notifying a caregiver of the movement for high risk patients. For example, using such a configuration of sensors, a nurse may be promptly warned that a patient 102 with an elevated risk of falling is in the process of getting out of bed, and thus the nurse can intervene to support the patient. Analogously, this configuration (and others described herein) can be used to issue an alert to warn to the patient himself if high risk motion is detected, thus allowing the patient to wait for help and/or stop the high risk motion.

While the example sensor arrangement 100 shows the plurality of motion/orientation sensors 104 connected to other sensors on a path and, ultimately, the motion tracking unit 106, via wires, this is not required. It is appreciated that in other examples, the motion/orientation sensors 104 may connect to the motion tracking unit 106, or a transceiver of a distributed computing system that is not disposed on the patient, via wireless connections.

Example Ambulatory Medical Device

In some cases, examples described herein can be worn by, attached, or otherwise connected to a patient for an extended period of time without substantial interruption. For example, the devices can be worn by, attached or otherwise connected to a patient for several hours, several days, several weeks, or longer. For example, the ambulatory device may be configured for substantially continuous monitoring and/or treatment over various periods of time, including at least a 24 hour period, at least a week, and at least a month. For example, such medical devices can include monitoring and/or treatment devices configured to continuously monitor a patient for certain medical conditions for extended periods of time, for example, for over 4 hours (e.g. treatment and monitoring devices such as sleep apnea devices), over 12 hours (e.g. treatment and/or monitoring devices such as mobile cardiac monitoring devices, wearable defibrillator devices, etc.), and including for substantially continuous monitoring over time periods over 24 hours or even several days. Such devices may monitor the patient substantially continuously, aside from periods during which the patient may periodically remove the device, such as for showering, refitting, changing a component of the device, etc.

Figure 2:
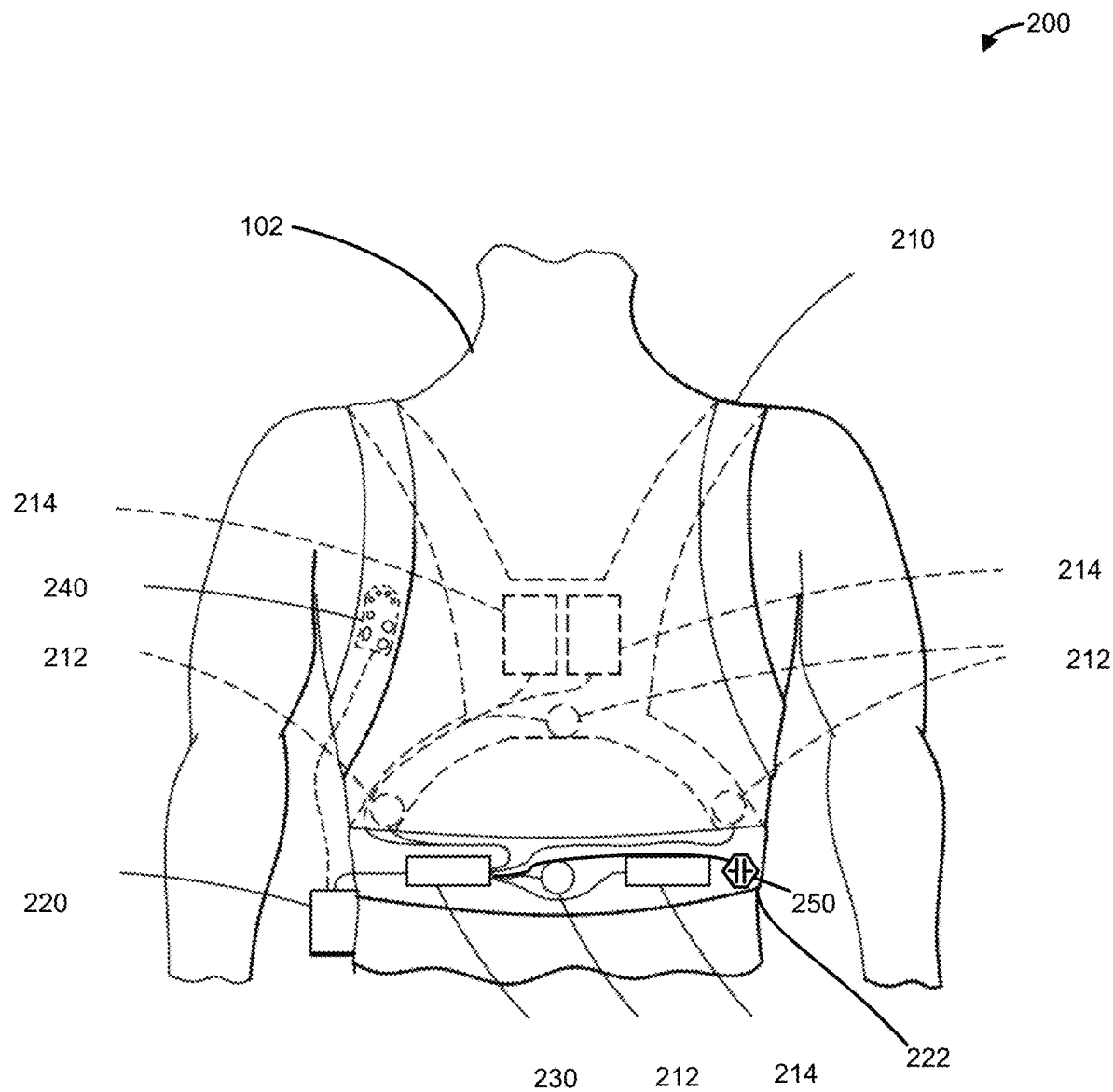
FIG. 2 is a schematic diagram of an ambulatory medical device in accordance with an example of the present disclosure.

FIG. 2 illustrates an example medical device 200 that is external, ambulatory, and wearable by the patient 102, such as the LifeVest® wearable defibrillator available from ZOLL® Medical Corporation. As shown, the medical device 200 includes a garment 210, a plurality of sensing electrodes 212, a plurality of therapy electrodes 214, a medical device controller 220, a connection pod 230, a patient interface pod 240, and a belt 222. A motion or orientation sensor (or more generally, an inertial measurement unit) 250 is also a part of the medical device 200, in this case attached to the belt 222.

The plurality of sensing electrodes 212 can be disposed at various positions about the patient's body (e.g., held in position by the garment 210 or adhesively attached to the patient's skin). As shown, the sensing electrodes 212 are electrically coupled to the medical device controller 220 through the connection pod 230. In some implementations, some of the components of the wearable medical device 200 are affixed to the garment 210 that can be worn on the patient's torso. For example, as shown in FIG. 2, the controller 220, at least some of the sensing electrodes 212, and, optionally, one or more therapy electrodes 214, which can attached to the patient via an adhesive, can be mounted on a belt 222 worn by the patient 102. The sensing electrodes 212 and the connection pod 230 can be assembled or integrated into the garment 210 as shown. The sensing electrodes 212 are configured to acquire signals descriptive of the cardiac function of the patient so that the controller 220 can monitor one or more cardiac signals of the patient. The plurality of therapy electrodes 214 can be electrically coupled to the controller 220 through the connection pod 230. The therapy electrodes 214 are configured to deliver one or more therapeutic defibrillating shocks to the body of the patient if the controller 220 determines that such treatment is warranted. The connection pod 230 may include electronic circuitry and one or more sensors (e.g., a motion or orientation sensor, an accelerometer, etc.) that are configured to monitor patient activity.

The wearable medical device 200 may include the optional patient interface pod 240 that is coupled to the medical device controller 220. For example, the patient interface pod 240 may include patient interface elements such as a speaker, a microphone responsive to patient input, a display, an interactive touch screen responsive to patient input, and/or physical buttons for input. In some implementations, these elements are incorporated into a housing of the controller 220. The patient interface pod 240 may be wirelessly coupled with the controller 220 through, for example, a network interface, thus transmitting electrocardiogram data to a separate and distinct medical monitoring device. The patient interface pod 240 may take other forms and include additional functionality. For instance, the patient interface pod 240 may be implemented on a smartphone, tablet, or other mobile device carried by the patient. In another example, the patient interface pod 240 may be worn as a watch about the wrist of the patient, or as a band about an upper arm of the patient. In some implementations, the controller 220 may communicate certain alerts and information and/or be responsive to patient input via patient interface elements included in the controller 220 and/or the patient interface pod 240. The patient and/or caregiver can interact with a touch display or the patient interface pod 240 to control the medical device 200.

In addition to accelerometers that may optionally be present on the wearable medical device 200 for the detection of heart sounds and other patient activity, the motion or orientation sensor 250 is also attached to the wearable medical device 200 in some examples. In some examples, the motion or orientation sensor 250 itself can be configured to detect heart sounds of the patient, and thus also act as a sensor for monitoring cardiac function and for measuring the physiologic status of the patient via heart and lung sounds. In some cases, these measurements are used in the treatment of the patient (e.g. defibrillation, cardiac pacing, CPR, treating dyspnea, heart failure, etc.). While the example in FIG. 2 shows the motion or orientation sensor 250 attached to the belt 222, the motion or orientation sensor 250 can be attached to other portions of the wearable medical device 200. The motion or orientation sensor 250 may include at least one of a three-dimensional accelerometer and a gyroscope so that the orientation of the patient 102 can be determined for both recording baselining or training data to populate data structures (which are described below with reference to FIG. 4) as well as for detecting and analyzing motion of the patient 102. Using at least one of a three-dimensional accelerometer and a gyroscope enables the wearable medical device 200 to detect motion primitives or motion sentences in which a torso (e.g., chest) or other body part (e.g. head, leg, shoulder, head, forearm, bicep, ankle, neck) of the patient 102 accelerates or changes orientation. Examples of motion primitives or sentences involving changes in torso motion and/or orientation and may include sitting up in bed, turning, some types of walking gaits, falling, swooning, and/or stumbling.

In other examples, the wearable medical device 200 can include a processor that is coupled to (or otherwise in communication with) the sensing electrodes 212 and the motion or orientation sensor (or inertial measurement unit) for monitoring patient movement during sleep. In monitoring patient movement during sleep, the processor can determine whether the patient movement is excessive using methods and systems described herein. For example, during a baselining or training period such as the first night of a patient wearing the wearable medical device 200, normal sleep movement may be recorded while a patient is sleeping. If employing template-based or heuristic, logic-based Motion Recognition, thresholds and/or rules may be established, based on this data acquired during the training period of what determines the motion Sentence, "Sleeping" (i.e.: "Lying quietly for sufficient period of time", which, in turn has the features: motion primitive, "Lying"; and motion adverbs, "Quietly" and "Sufficient Period of time"). For instance, a threshold for the angular position of the patient's torso may be predefined as 15 degrees or less, or may be adjusted by the caregiver during the baselining process to fit the specific situation of the patient, e.g., to note that the patient likes to sleep with extra pillows or the head of the bed raised. Similarly, levels of activity may be determined, for instance, "Sleeping soundly", "Active Sleeping", or "Waking Sleeping" based on the activity during sleep and, in some cases a classification by the caregiver or other person reviewing the training period measurements. In cases where a HMM or Deep Learning Network is used for Motion Recognition, the data recording during the baselining or training period for that particular patient will improve the accuracy of the Motion Recognition. Time of day may also be included as a data element in the motion vector to enhance accuracy, since there will be a higher likelihood of sleep, for most individuals, during the nighttime hours.

Types of movements monitored and classified include, but are not limited to leg, arm, head, and torso movements, as well as the directions and patterns of movements). Thresholds of normal sleep movement (for example the frequency of movement, the amplitude of movement) can be established and used to classify patient movement and/or trigger actions. In addition to these applications, the processor may also be configured to alter a cardiac arrhythmia treatment protocol in response to classifying the patient movement as excessive. For example, in some implementations a treatment protocol may associate a confidence score with a detected arrhythmia condition. In situations where the processor determines that the patient movement is excessive (e.g., the movement transgresses predetermined threshold amounts of movement and/or duration of such movements), the treatment protocol may associate a lower confidence score with the detected arrhythmia condition than the protocol would in the absence of such movement. In some implementations, a defibrillation current to be applied to the patient may be delayed for a period of time to allow for an improvement in the confidence score. Alternatively or in addition, an altered defibrillating current can be applied to the patient based on the type or degree of excessive movement during sleep, as determined by the processor. Furthermore, the processor may also alter the arrhythmia treatment protocol by prepending one or more additional alerts, warnings, and/or notifications (e.g., a tactile alert to the patient, an alert to hospital personnel, etc.) to a default arrhythmia treatment protocol.

Patient movement can be classified, using methods and systems described herein, as either excessive or not excessive using, in some examples, the thresholds. In other words, the frequency, magnitude, duration, portions of the body, and combinations thereof can be classified in light of the motion data acquired while the patient is sleeping during the baselining or training period. For example, a magnitude of patient movement can be compared to a corresponding threshold set by a health care provider. In another example, a frequency of patient movement can be compared to a corresponding threshold set by a health care provider. In yet another example, a duration of patient movement can be compared to a corresponding duration threshold set by a health care provider. Any or all of these example thresholds, when exceeded, can trigger an action, for example, alerting a health care provider of the excessive movement via a notification component.

Figure 3:
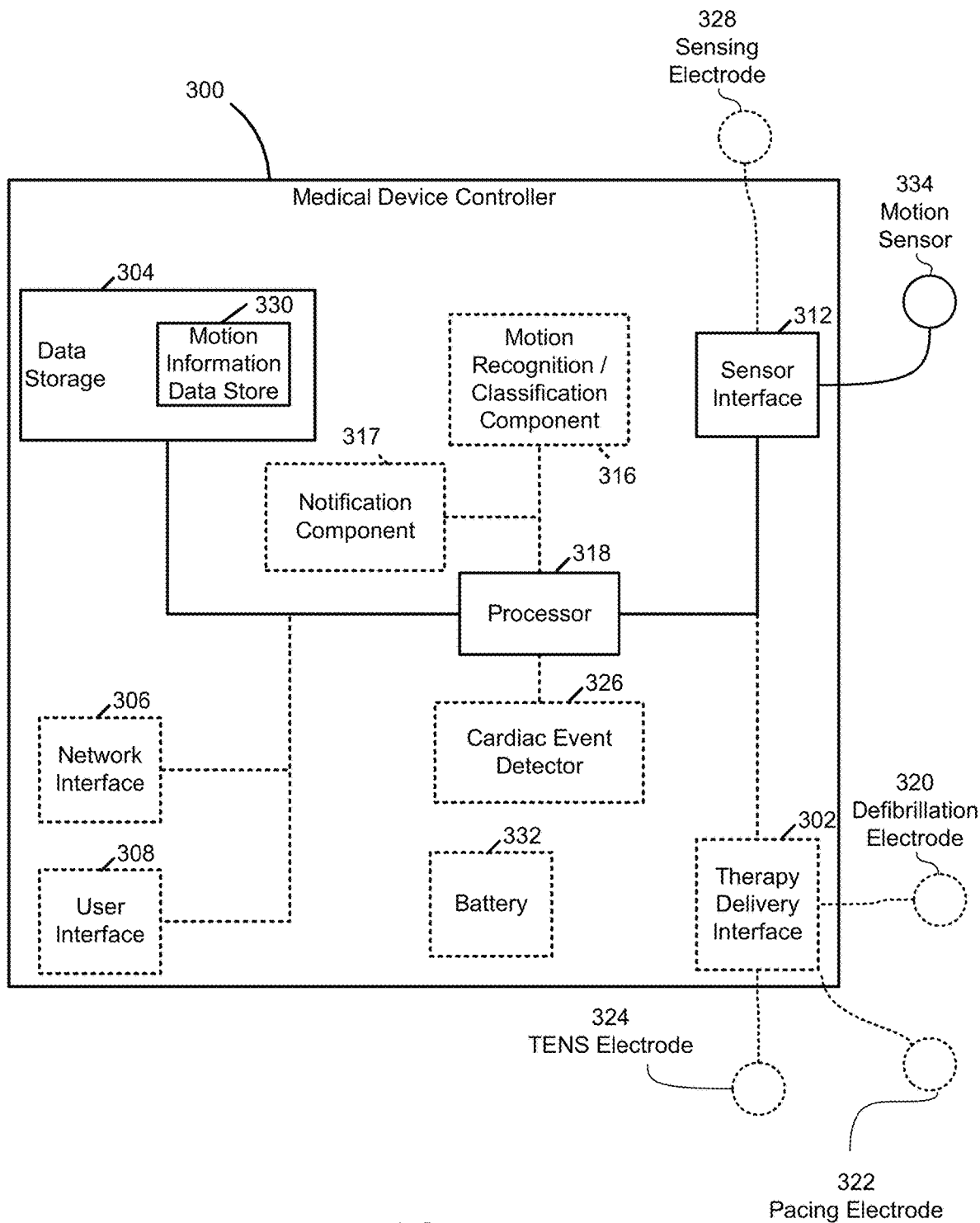
FIG. 3 is a schematic diagram of a medical device controller in accordance with an example of the present disclosure.

FIG. 3 shows a schematic of an example of a medical device controller 300 that receives motion or orientation sensor data and stores the data for classification according to methods and systems described herein. Optional components of the medical device controller are rendered in FIG. 3 using dashed lines. The medical device controller 300 is, in some examples, incorporated into the motion tracking unit 106 or the controller 220.

The medical device controller 300 includes an optional therapy delivery interface 302, data storage 304 (which includes motion information data store 330 that is described below with reference to FIG. 4), an optional network interface 306, an optional user interface 308, a sensor interface 312, an optional motion recognition classification component 316, an optional notification component 317, at least one processor 318, and an optional battery 332.

The therapy delivery interface 302 (if included) may be coupled to one or more electrodes configured to provide therapy to the patient including, for example, one or more defibrillation electrodes 320, pacing electrodes 322, and/or TENS electrodes 324. The sensor interface 312 and the therapy delivery interface 302 may implement a variety of coupling and communication techniques for facilitating the exchange of data between the sensors 212, sensing electrode 328, and motion sensor 334, the therapy delivery devices 320, 322, and 324, and the medical device controller 300. In some examples, the one or more motion/orientation sensors 334 include one or more of the motion/orientation sensors 104 and/or the motion or orientation sensor 250. Also, in some examples, the therapy delivery devices 320, 322, and 324 are included in the therapy electrodes 214.

The data storage 304 includes one or more of non-transitory computer readable media, such as flash memory, solid state memory, magnetic memory, optical memory, cache memory, combinations thereof, and others. The data storage 304 is configured for storing executable instructions and data used for operation of the medical device controller 300 itself as well as operation of one or more of the sensor arrangement 100, the motion tracking unit 106, and the wearable medical device 200 in various examples. Furthermore, as will be explained below in more detail, the data storage 304 includes the motion information data store 330. The motion information data store 330 includes patient motion data collected by and transmitted from the one or more motion/orientation sensors 334. The motion information data store 330 contains the information necessary for the measurement of motion and the detection and estimation of at least one of a motion primitive, motion modifier, motion object, motion grammar and motion sentence. Motion primitive, motion modifier, motion object, motion grammar are all termed "motion sentence features". In the case of a template-based or heuristic Motion Recognition system, this may include thresholds and other logic-based elements and data structures. In the case of a Deep Learning Network, this may be node coefficients. In the case of HMM approaches, this may be in the form of state transition probabilities. The motion information data store 330 may also include data acquired during the baselining or training period or derived at least in part from data acquired during the baselining or training period. Motion data corresponding to predetermined motion sentence features and motion sentences that are used to classify inbound motion data from the one or more motion/orientation sensors 334 while a motion classification component of the medical device controller is operating in monitoring mode, is described further below.

In some examples, the network interface 306 can facilitate the communication of information between the medical device controller 300 and one or more other devices or entities over a communications network. For example, where the controller 300 is included in an ambulatory medical device (such as medical device 200), the network interface 306 may be configured to communicate with a medical device controller 300 included within a hospital medical device, such as the hospital medical device 1316 described further below with reference to FIG. 13. In another example, the network interface 306 may be configured to communicate with a remote device that includes a processor, such as the programmable devices described further below with reference to FIG. 13, on which a caregiver can access information related to the patient.

In some examples, the optional user interface 308 includes one or more physical interface devices such as input devices, output devices, and combination input/output devices and a software stack configured to drive operation of the devices. These user interface elements may render visual, audio, and/or tactile content, including content relating to location-specific processing. Thus the user interface 308 may receive input or provide output, thereby enabling a user to interact with the controller 300.

The sensor interface 312, in addition to being coupled to the one or more motion/orientation sensors 334 may be coupled to any one or combination of sensing electrodes/other sensors to receive other patient data indicative of patient parameters. Once data from sensors has been received by the sensor interface 312, the source sensor is identified by the processor 318 and the data is transmitted to an appropriate component within the medical device controller 300. For example, if heart data is collected by a cardiac sensing electrode 212 and transmitted to the sensor interface 312, the sensor interface 312 will transmit the data to the processor 318 which, in turn, relays the data to the cardiac event detector 326.

In some implementations, the processor 318 includes one or more processors that each are configured to perform a series of instructions that result in manipulated data and/or control the operation of the other components of the controller 300. In some implementations, when executing a specific process as provided herein (e.g., FIGS. 5 and 6), the processor 318 is configured to make specific logic-based determinations based on input data received, and further capable of providing one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In this sense, the structure of processor 318 according to one example is defined by the flow charts shown in FIGS. 5 and 6. In some example cases, the processor 318 proceeds through a sequence of logical transitions in which various internal register states and/or other bit cell states internal or external to the processor 318 may be set to logic high or logic low. This specific sequence of logic transitions is determined by the state of electrical input signals to the processor 318 and a special-purpose structure is effectively assumed by the processor 318 when executing each software instruction of the software process shown in FIGS. 5 and 6. Specifically, those instructions anticipate the various stimuli to be received and change the implicated memory states accordingly. In this way, the processor 318 may generate and store or otherwise provide useful output signals. It is appreciated that the processor 318, during execution of a process, is capable of processing specific input signals and rendering specific output signals based on the one or more logic operations performed during execution of each software instruction. As referred to herein, the processor 318 is configured to execute a function where software is stored in a data store coupled to the processor 318 that is configured to cause the processor 318 to proceed through a sequence of various logic decisions that result in the function being executed. The various components that are described herein as being executable by the processor 318 may be implemented in various forms of specialized hardware, software, or a combination thereof.

In some examples, the controller 300 includes a cardiac event detector 326 to monitor the cardiac activity of the patient, identify cardiac events experienced by the patient based on received cardiac signals, and, if necessary, treat the patient by executing a treatment protocol that may culminate in the delivery of one or more defibrillating shocks to the body of the patient.

Figure 5:
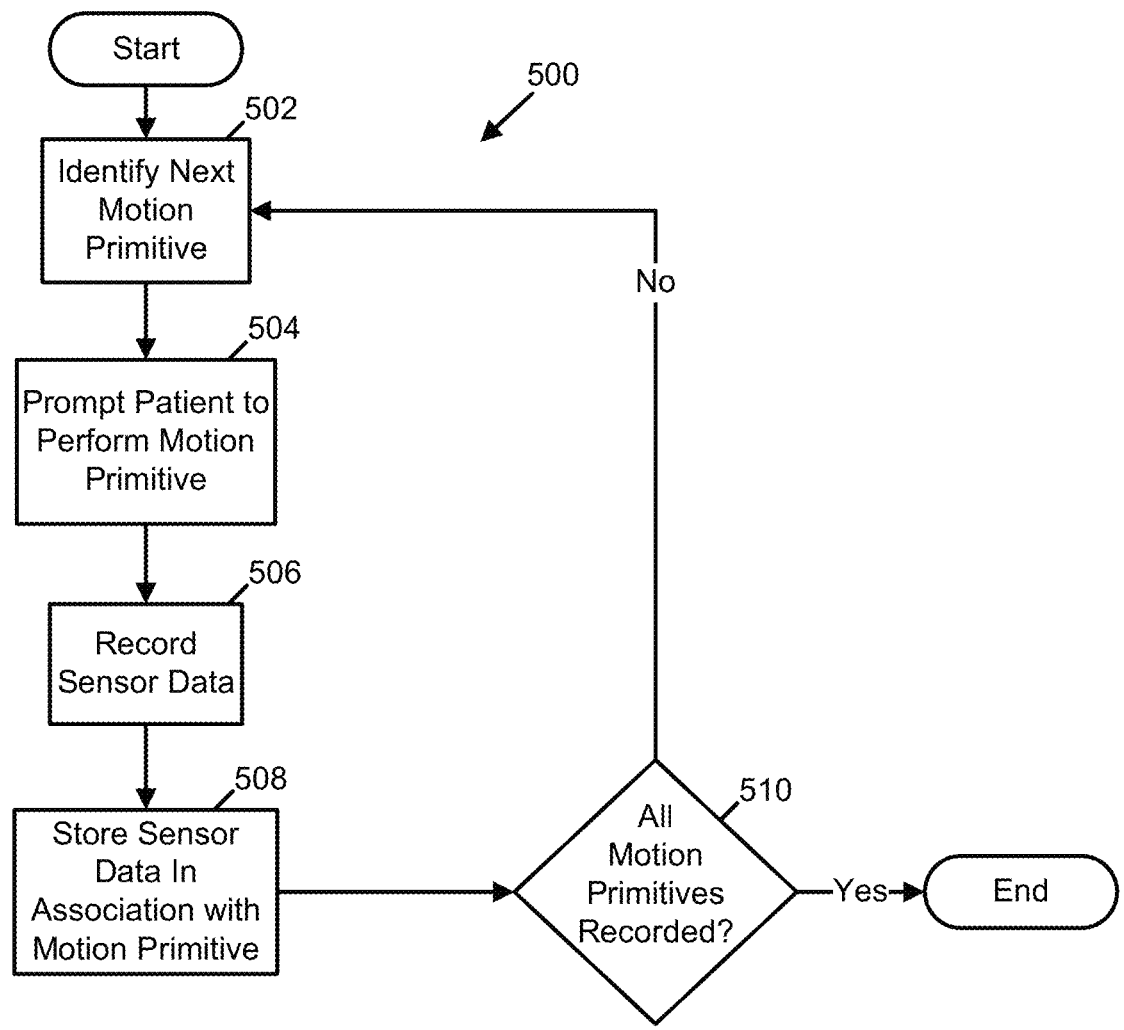
FIG. 5 is a flow diagram illustrating a baselining/training process that a motion recognition or classification component is configured to execute when operating in the baselining/training mode in accordance with an example of the present disclosure.
Figure 6:
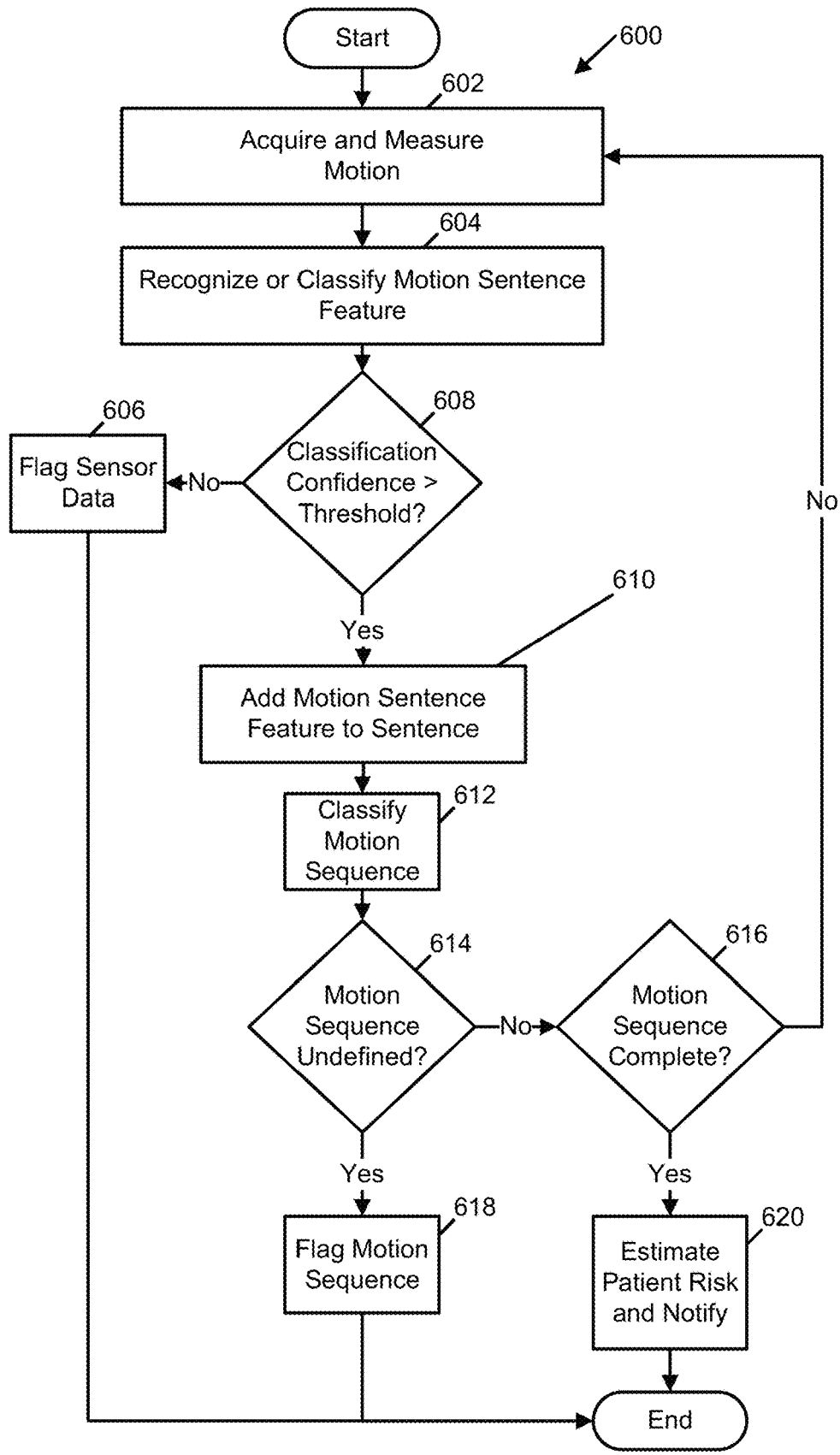
FIG. 6 is a flow diagram illustrating a method for detecting motion of a patient and classifying the detected motion as corresponding to a motion primitive or a sequence of multiple motion primitives in accordance with an example of the present disclosure.

In some examples, the optional motion recognition or classification component 316 is configured to receive and process motion information acquired by the one or more motion/orientation sensors 334. In some examples, the motion recognition or classification component 316 is configurable to operate in a baselining/training mode and/or a monitoring mode. FIG. 5 illustrates one example of a baselining/training process that the motion recognition or classification component 316 is configured to execute when operating in the baselining/training mode. FIG. 6 illustrates one example of a motion classification process that the motion recognition or classification component 316 is configured to execute when operating in the monitoring mode. The motion recognition or classification component 316 is illustrated as optional because, in some examples (e.g., the example illustrated in FIG. 13), the motion recognition or classification component 316 is implemented on a distinct programmable device (e.g., the server 1302). Where the motion recognition or classification component 316 is implemented by a device other than the medical device controller 300, the processor 318 stores inbound sensor data in the motion information data store 330 (e.g., in the sensor data structure 400) prior to transmitting the sensor data to the remote motion classification component via, for example, the network interface 306. In some examples, the motion recognition or classification component 316 is configured to determine locations of medical devices using techniques described in U.S. patent application Ser. No. 15/077,995, titled SYSTEMS AND METHODS OF DETERMINING LOCATIONS USING A MEDICAL DEVICE, filed Mar. 23, 2016, and published as U.S. Publication No. US20160278652A1, which is hereby incorporated herein by reference in its entirety.

In some examples, the optional notification component 317 is configured to receive and process one or more notification requests from the motion recognition or classification component 316 should the motion recognition or classification component 316 determine that an alert, warning, or other notification is warranted in response to a detected sequence of patient motion. When executing according to its configuration, the notification component 317 may issue notifications via the network interface 306 and/or the user interface 308. For example, the notification component 317 may transmit one or more instructions to a programmable device (e.g., the client device 1304 described below with reference to FIG. 13) and/or a medical device (e.g., any of the medical devices 1316, 1314, 1312, 1310, 1308 described below with reference to FIG. 13) to issue an alert to a caregiver (e.g., the caregiver 1319 described below with reference to FIG. 13) via a user interface of the programmable device. Alternatively or additionally, the notification component 317 may present a notification to the patient 102 via the user interface 308. These notifications may include visual, audio, and tactile components.

In some implementations, in addition or alternative to notification actions, the notification component 317 may be configured to store the output of the motion recognition or classification process in one or more databases. In such cases, the data can be grouped by type of motion data, date and time of day that the data was collected, and/or annotation of the data based on analysis of the information. An authorized person such as a caregiver or support personnel may cause the medical device to generate one or more reports based on the data. For example, such reports may be ordered by the type of data, and date and time of day the data was collected.

In various implementations, the controller 300 implements an embedded operating system that supplies file system and networking support. In one example, the controller 300 includes software features that provide relational database functionality, touch screen display drivers, audio generation, BLUETOOTH wireless networking, BLUETOOTH Low Energy (BLE) Beacon technology (including, but not limited to, iBeacon, or near-field communication methods such as active NFC beacons or passive, contactless RFID tags), networking security and firewalling, and data encryption services.

The motion information may be augmented by location beacons placed at junctures within the facility such as a hospital, for example at the ends of hallways, mid-corridor locations, within stairwells, cafeteria and entrances of the hospital and the door of the patient's room. The location beacon may be implemented with a near-field beacon such as iBeacon, which will communicate with the device on the patient as they are walking by and provide absolute location position data which the device can use to calibrate its position as well as transmit its actual location to caregivers. By combining the motion/orientation sensors with the beacon system, the number of beacons can be reduced, thus saving cost and complexity of implementation.

Figure 4:
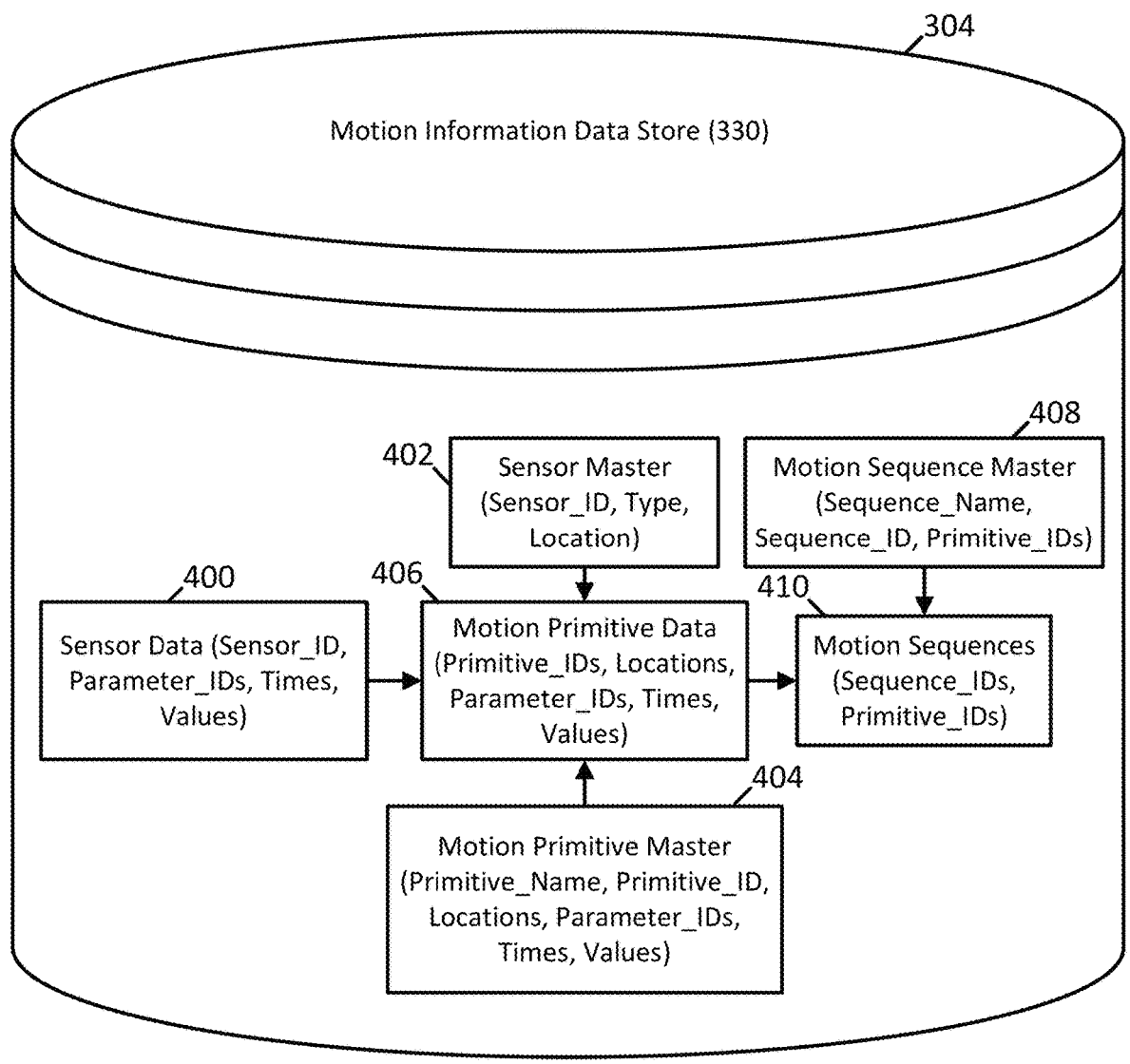
FIG. 4 is a schematic illustration of a motion information data store of the medical device controller of FIG. 3 in accordance with an example of the present disclosure.

FIG. 4 illustrates an example of the motion information data store 330 for storing a plurality of motion parameters and shown as a component of the data storage 304 of the medical device controller 300. The motion information data store 330 includes a sensor data structure 400, a sensor master structure 402, a motion primitive master structure 404, a motion primitive data structure 406, a motion sequence master structure 408, and a motion sequences structure 410. In some examples, the data structures 402, 404, and 408 are populated by the motion recognition or classification component 316 while operating in baselining/training mode (e.g., during an initial fitting of a medical device including the medical device controller 300). In some examples, the data structures 400, 406, and 410 are populated by the motion recognition or classification component 316 when operating in a monitoring mode.

The sensor master structure 402 stores a list of motion/orientation sensors (e.g., the one or more motion/orientation sensors 334) that acquire and transmit motion data to the processor 318 via the sensor interface 312. Examples of types of sensors represented in the sensor master structure 402 include, but are not limited to, one or more of one-dimensional accelerometers, two-dimensional accelerometers, three-dimensional accelerometers, gyroscopes, and magnetometers. As shown in FIG. 4, the sensor master structure 402 includes at least two parameters, including a sensor_ID field and a location field. The sensor_ID field is configured to store an identifier of each the one or more motion/orientation sensors 334. These identifiers are used throughout the data model illustrated in FIG. 4 to associate data with the identified sensor. The location field is configured to store data descriptive of an anatomical location on the body of the patient 102 where the sensor identified by the sensor_ID is positioned. Thus, the data stored in the location field associates a sensor with a location on the body of the patient 102 (e.g., a left forearm, a right forearm, a left shin, a right thigh, a crown of a head, a thorax). This location data is then used by other elements of the motion information data store 330 and the medical device controller 300 (e.g., the motion recognition or classification component 316) to identify motion primitives and optionally motion sentences performed by the patient 102. The sensor master structure 402 improves the computational efficiency of the medical device controller 300 because information that does not change frequently (e.g., sensor location) is not transmitted with each datum of motion data. In some examples, the sensor master structure 402 is populated with actual sensor IDs and anatomical locations during an initial fitting of a sensor arrangement (e.g., the sensor arrangement 100) or an ambulatory medical device (e.g., the ambulatory medical device 200).

The motion primitive master structure 404 stores baseline data descriptive of various predetermined motion primitives recorded by the medical device controller 300 as the motion primitives are performed by the patient 102. As stated above, a motion primitive is essentially the "verb" of a motion sentence containing motion sentence features. A motion primitive is a predefined motion that is often simple enough or common enough that it can be performed by the patient 102 upon command, so as to collect corresponding patient-specific baseline data during the baselining/training period. The motion primitive may also be identified as a component of a more complicated movement that includes other predetermined motion sentence features in one or more motion sentence. Examples of motion sentences that are particularly helpful in a clinical healthcare setting (e.g., a hospital or in-patient clinic) are, among others: 1) "Standing up from a bed"="Sitting up in bed"+"Bringing legs over edge of bed."+"Putting feet on floor."+"Bending over and standing up."; 2) "Sitting down onto a bed."; 3) "Sitting up in bed from a supine position."; 4) "Laying down in bed from a sitting position."; 5) "Taking a step by leading with a left foot."; 6) "Taking a step by leading with a right foot."; 7) "Opening a door."; 8) "Turning around while standing in place."; 9) "Sleeping soundly."; and 10) "Sitting down in a chair or on a toilet from a standing position.". Any one or more of these example motion primitives and motion sentences, or other motion primitives motion sentences and motion sentence features not explicitly identified here, are recorded for individual patients (such as patient 102) wearing the motion or orientation sensor assembly 100 or the ambulatory medical device 200 so that variations and features of the motion specific to the individual patient and the individual motion/orientation sensors or their locations are reflected in the baseline data recorded during a baselining/training period.

These motion primitives, among others, can be recorded and analyzed for each individual patient while the medical device controller 300 is operating in a baselining/training mode as described below in FIG. 5, thus creating a library of baseline data as well as improvements to the motion recognition algorithm accuracy for that particular patient. Data from the motion/orientation sensors are measured and input into the motion recognition algorithm while the medical device controller 300 is operating in a monitoring mode. The motion recognition algorithm classifies the movement so that it best corresponds to a predetermined motion primitive or motion sentence feature. The outputs of the motion recognition (MR) process (e.g. motion primitive, modifiers, objects, adjectives, and grammatical structure) may then be analyzed to determine whether the MR outputs pose a threat to the health or safety of the patient, or otherwise constitute an incipient hazard. A notification component (such as an alarm or notification to a health care provider or other caregiver) may then be executed in response to the classification of the detected motion. An appropriate signal can be provided to one or more of the patient 102, a health care provider, or a component of a medical device system, any one of which can initiate an action. These actions may include preventive measures, should the sequence of motions primitives anticipate a hazardous consequence of the patient motion.

As shown in FIG. 4, the motion primitive master structure 404 includes a primitive_name field, a primitive_ID field, a locations field, a parameter_IDs field, a times field, and a values field. The primitive_name field is configured to store data descriptive of a human readable name for each motion primitive to be recorded for the patient 102. The primitive_ID field is configured to store an identifier of each motion primitive. These identifiers are used throughout the data model illustrated in FIG. 4 to associate other data with the identified motion primitive. The remaining four fields: the locations field, the parameter_IDs field, the times field and the values field are configured to store sensor data acquired during the recordation of each motion primitive. More specifically, each motion primitive may consist of one or more sensor values (as specified in the values field) of parameters (as identified in the parameter_IDs field) recorded at anatomical locations (as specified in the locations field) at particular times (as specified in the times field). The motion primitive master structure will also contain information descriptive of motion objects and motion modifiers.

The motion sequence master structure 408 stores data descriptive of motion sentences—both single motion sentences as well as sequences of motion sentences. Examples of names of motion sentences include: "Step right foot."; "Sit up in bed."; "Turn around (while standing)."; "Sit down (from standing.)"; and other such examples. A sequence of motion sentences may describe more complex movements of the patient. Examples of such sequences include a patient getting out of the bed to visit the bathroom, a patient leaving their room and walking down a corridor, and a patient performing a six-minute walk test (which can be used as patient-specific baseline data obtained during a baselining/training period to identify progressively less stable walking over time). As shown in FIG. 4, the motion sequence master 408 includes a sequence_name field, a sequence_ID field, a primitive_IDs field, and an action field. The sequence_name field is configured to store data descriptive of a human readable name for each motion sentence associated with the patient 102 while the patient is being monitored by a medical device including the medical device controller 300. Examples of names of sequences of motion sentences include: "Visit the bathroom."; "Perform a six-minute walk test."; "Visit the nurse's station."; and other such example. Each sequence is thus composed of two or more motion sentences that, together, are descriptive of the overall sequence activity.

The sequence_ID field is configured to store an identifier of each motion sequence. These identifiers are used throughout the data model illustrated in FIG. 4 to associate other data with the identified motion sequence. The primitive_IDs field is configured to store one or more primitive_IDs that together constitute the motion sequence identified in the sequence_ID field. The action field is configured to store data that identifies one or more actions to trigger in response to identifying the motion sequence identified by the sequence_ID. Actions identifiable via this field in some examples include executing a notification component, which is automation designed to address the consequences of the detected motion. For example, a notification component may be executable by a processor and be configured to issue an alert to a device associated with a user or stationed at a particular location, as described further below with reference to FIG. 13.

The action field may also be configured to include various conditions that influence when and which of the one or more actions are triggered. For example, an age of the patient, a current time of day (including a day/night designation as well as an hour) associated with the motion, the operating mode of the motion classification component, and/or action to be executed can be included in the action field. For example, an alert is transmitted to a pager of a dedicated nurse making rounds for a 90 year old patient during the day time when the patient gets out of bed. A similar alert may be triggered and transmitted to a nursing station during a more lightly staffed night shift. Alternatively, no alert is triggered for a 20 year old patient regardless of the time of day this patient gets out of bed.

The sensor data structure 400 stores various data descriptive of patient motion acquired by each motion or orientation sensor while the medical device controller 300 is executing the monitoring mode. As shown in FIG. 4, the sensor data structure includes a sensor_ID field, a parameter_ID field, a time field and a value field. The sensor_ID field is configured to store an identifier of a motion or orientation sensor defined in the sensor master structure 402. The parameter_ID field is configured to store data that specifies the identity of a parameter measured by the data values acquired by the sensor identified in the sensor_ID field. For example, force data in an x-axis direction, a y-axis direction, and a z-axis direction will each have different parameter IDs that specify the direction of force. Similarly, orientation (e.g., tilt, rotation) data transmitted by a gyroscope will have one or more parameter IDs used to identify the measurement corresponding to the data. The time field is configured to store data that indicates a point in time at which each measured value is acquired by the one or more motion/orientation sensors and/or a duration over which a movement occurs. The time field of the sensor data structure 400 is used as an index to place sensor data collected for the patient 102 into an order so that multiple motions can be analyzed to determine a motion sentence or multiple motion sentences can be stringed into a motion sequence and also to measure a duration of a motion (e.g., when a motion starts and stops). The values field is configured to store values parameter measurements acquired by motion/orientation sensors. These values may be, for example, scalar or vector values measured by a motion or orientation sensor as descriptive of the motion of the patient 102. It is appreciated that scalar values can be associated with one or more vector components when analyzed in conjunction with one or more of sensor_ID, parameter_ID, and other data structures and/or elements of the motion information data store 330.

The motion primitive data structure 406 stores data descriptive of motion primitives and other motion sentence features exhibited within the sensor data stored in the sensor data structure 404. As shown, the motion primitive data structure 406 includes a primitive_IDs field, a locations field, a parameter_IDs field, a times field, and a values field. In some examples, data stored in these fields is determined by joining the data stored in the sensor data structure 400 with the data stored in the sensor master structure 402 and identifying primitive_IDs from the motion primitive master structure 404 having associated locations, parameter_IDs, times, and values that match locations, parameter_IDs, times, and values within the joined data. The confidence required to find a match may vary between examples.

The motion sequences structure 410 stores data descriptive of motion sentences and sequences of motion sentences exhibited within the motion primitives stored in the motion primitive data structure 406. As shown, the motion sequences structure 410 includes a sequence_ID field and a primitive_IDs field. In some examples, data stored in these fields is determined by joining the data stored in the motion primitive data structure 406 with the data stored in the motion sequence master structure 408 and identifying sequence_IDs from the motion sequence master structure 408 having associated primitive_IDs that match primitive_IDs within the joined data. The confidence required to find a match may vary between examples. It is appreciated that, in some examples, the motion primitive data structure 406 and the motion sequences data structure 410 may be implemented as views into the sensor data structure 400 rather than data stores including copies of the data.

A state space may be defined where there are two or more relevant patient motion states. These patient motion states may correspond to one or more motion primitives as described herein. Example patient motion states are presented below for illustration purposes only and some deviation of the stated measurements can be expected in various examples.

Patient Sitting: Inactive—The patient torso is inclined at an angle greater than 15 degrees, but with movement velocity of less than 1 ft/sec (or other appropriate threshold, e.g. 0.25, 0.5, 2, 4, 8 or 16 ft/sec) in a rolling period of five seconds. In other examples, the Patient Sitting: Inactive definition may be based on other motion measurements, such as root mean square (RMS) movement, acceleration, etc., or a multifactorial combination thereof. The Patient Sitting state may also have a sub-state of "Active" in which the movement velocity is greater than that defined for the "Inactive" state.

Patient Sleeping: Inactive—The patient is inclined at less than 15 degrees, but with a movement velocity of less than 0.25 ft/sec in the last ten minutes (or other thresholds, ranges, parameters measured as above).

Patient Sleeping: Active—The patient is inclined at less than 15 degrees, but with a movement velocity of more than 0.25 ft/sec in a rolling period of the most recent ten minutes (or other thresholds, ranges, parameters measured as above).

Patient Getting Out of Bed—This state is preceded by either one of Patient Sleeping: Inactive or Patient Sleeping: Active. The patient is inclined at greater than 15 degrees. The Patient Getting Out of Bed state may be further subdivided into states of "Sitting Up" where the torso is in the process of inclining upward toward a vertical position; "Putting Feet Down", where the motion/orientation sensor 104 located on the patient's foot or ankle descends downward for more than 6 inches. In some examples, "Patient Stepping Onto Floor" is indicated when the motion or orientation sensor located on either the patient's thigh or torso becomes vertically aligned to the foot sensor to less than 0.5 feet.

Patient Sleeping: Rolling Over—The Rolling Over sub-state of Patient: Sleeping is defined when the angular rotational movement of the torso exceeds 20 degrees of rotation (while still remaining at an angle of less than 15 degrees relative to the horizontal.) If Patient Sleeping: Rolling Over is detected, then the device may determine that physiologic monitoring sensors (e.g. ECG, SpO2, etc.) may now be on the underside of the patient and compressed between the patient and the mattress. In response, a different set of sensors can be activated having locations that facilitate monitoring patient physiologic metrics more accurately (e.g., because they are not compressed between the patient and a bed). For instance, the ZOLL LifeVest® wearable defibrillator includes two sets of ECG electrode pairs connected to two ECG leads: the Front-Back (FB) and the Side-to-Side (SS) lead pairs. If it is determined that the patient is lying on a side, then the processor would switch to monitor the SS leads rather than the FB leads, or alternatively might perform some additional processing such as signal filtering with the expectation that there will be higher compression and motion artifact on the FB lead.

Patient Standing Up—Similar to the Patient Getting Out of Bed state, but preceded by a Patient Sitting state rather than a Patient Sleeping state.

Patient Standing—Patient torso is less than 5 degrees relative to vertical, but horizontal motion movement velocity of less than 1 ft/sec (or other appropriate threshold, e.g. 0.25, 0.5, 2, 4, 8 or 16 ft/sec) in a most recent period of rolling five seconds.

Patient Falling—The prior state is Patient Standing, or Patient Sitting, in which angular velocity to the horizontal exceeds 10 degrees per second.

Patient Walking—Patient torso is less than 5 degrees relative to vertical, but horizontal motion movement velocity of more than 1 ft/sec (or other appropriate threshold, e.g.

0.25, 0.5, 2, 4, 8 or 16 ft/sec) in the most recent rolling period of five seconds. Techniques may be used, known to those skilled in the art, such as zero-velocity updates (ZUPT) or Zero-Velocity Detection (ZVD), whereby a state machine determines when the particular motion/orientation sensor 104 on the patient has ceased movement for a duration of time sufficient to perform a calibration. The intervals may be regular or irregular. For instance, the calibration may be based on a known state of motion, e.g. "Patient Walking," in which case it may base the motion estimation primarily on the motion/orientation sensor 104 located on the patient's foot or ankle, and the calibration may occur upon zero velocity detection when the patient places that particular foot on the ground with each step, using such algorithms as described by Skog, et al (I. Skog, P. Handel, J.-O. Nilsson, and J. Rantakokko, "Zero-velocity detection—an algorithm evaluation," IEEE Trans. Biomed. Eng., vol. 57, no. 11, pp. 2657-2666, November. 2010, which is hereby incorporated herein by reference in its entirety.) According to Skog, et al: "Even though the motion information provided by the foot mounted inertial sensors are used for different purposes in the gait analysis and the pedestrian navigation, both application fields require motion information of a high quality."

Skog et al further describes "that for inertial navigation systems (INSs) employing low-cost sensors, the position error is proportional to the cube of the operation time. Therefore, with the performance of the low-cost inertial sensors currently available, free-inertial navigation is only feasible for time periods in the range of a few seconds. However, the cubic-error growth can be reduced by imposing constraints on the navigation solution using information about the system dynamics. A type of information commonly used for this purpose is knowledge about the time epochs when the system is in a stationary phase, i.e., when the system has a constant position and attitude. Using this information to bound the error growth is referred to as using zero-velocity updates. Zero-velocity updates are well suited for bounding the error growth of a foot-mounted INS, as during ordinary gait the foot returns to a stationary state on a regular base."

Skog et al further explains that "in foot-mounted, inertial sensor based pedestrian navigation systems, where the accumulated motion of the foot over several steps is of interest, "soft" zero velocity updates are commonly used. That is, the knowledge of when the system has zero velocity is used together with a model for how the position, velocity, and attitude errors develop with time, to provide an estimate of the accumulated errors since the last zero-velocity update. The estimate of the accumulated errors is then fed back to correct the navigation solution and calibrate the navigation algorithm."

Skog et al describes "hard" zero velocity updates as follows: "In the gait analysis, where the motion of the foot during the individual gait cycles, but not the accumulated motion of the foot over several cycles, is of interest, "hard" zero-velocity updates are commonly used. The updates are hard in the sense that when the system imposes a zero-velocity update, the position, the velocity, and the yaw are reset to zero, and the roll and pitch are initialized directly from the accelerometer readings of the gravity acceleration."

A calibration of motion/orientation sensors 104 may also be performed while the device appears to be inactive from the user's perspective (e.g., during any of the inactive sub-states (like "Patient Sleeping: Inactive" or "Patient Resting: Inactive"), but is actually executing various self-tests that do not require user or patient intervention. During these periods of inactivity, the calibration intervals may be as frequent as every 1 millisecond, but may be as long as once every 1 minute or once every 3 hours. The calibration may last for some time period, such as 1 second, 1 minute, 1 hour, etc. during which time such time-dependent factors as offset drift can be estimated.

During these calibrations, such motion features as RMS noise, offset and drift may be estimated. The updated estimate of RMS noise can be used for determining the threshold for detection of the zero-velocity state. The updated estimates of offset and offset drift can be used to reduce the final positional accuracy to approximately 1% of the total distance traveled, e.g. for every 30 feet of travel, the error would be approximately 3.5 inches.

Example Motion Classification Processes

FIG. 5 is a flow diagram illustrating a patient-specific baselining/training process 500 for collecting baseline data corresponding to motion primitives, motion sentence features, motion sentences and specific sequences of motion sentences. The patient-specific baselining/training process 500 may be performed by a medical device including the medical device controller 300 or another programmable device including a motion recognition or classification component 316. The motion recognition or classification component 316 may be operating in a patient-specific baselining/training mode. The patient-specific baselining/training process 500 begins by positioning one or more motion/orientation sensors (e.g., the one or more motion/orientation sensors 334) on a patient (e.g., the patient 102) and recording the position of each of the one or more sensors in the sensor master structure 402. This recordation may be performed by default or by affirmative assignment of locations to sensors via a user interface. If default locations for the one or more sensors are not modified via the user interface, the location data stored in the sensor master structure 402 may require that particular sensors be placed on the patient 102 at particular locations. In some examples, the sensors include visual indicia of the proper anatomical location for a sensor.

The patient-specific baselining/training process continues with identifying 502 a motion primitive to be performed by the patient so that corresponding baseline data can be collected and analyzed. The identified 502 motion primitive can be any of the examples presented above or other motion primitives used to identify and classify patient motion. The patient is then prompted 504 to perform the motion primitive. This prompting 504 can be provided directly to the patient 102 by the medical device (or a similar device in communication with the motion information data store 330) or by a caregiver using the medical device to collect baseline data. Upon the patient 102 performing the motion primitive, a motion or orientation sensor (e.g., the one or more motion/orientation sensors 334) attached to or worn by the patient 102 records 506 sensor data corresponding to the motion primitive. The sensor data is then stored 508 in association with the identified 502 and performed 504 motion primitive, for example in the motion primitive master structure 404. This establishes baseline data corresponding to the identified 502 and performed 504 motion primitive, including motion objects, modifiers, sentences and sequences of motion sentences.

Next, the baselining/training process 500 determines whether baseline data for all motion primitives requested or recommended for the patient have been recorded 510. A list of all motion primitives requested or recommended to be recorded may be identified for patient 102 based on various health factors, such as age, weight, height, health risks (disorientation, fatigue, memory loss, fainting, etc.), type of illness, type of surgery or procedure to be performed or previously performed, and others. Still others may be requested as part of a standard process to monitor patient motion and used determine deviations from normal motion (e.g., to determine a seizure, determine coughing, determine shivering). If all of the motion primitives requested or recommended for the patient have been recorded, the method 500 ends. If some motion primitives remain to be recorded 510, the patient-specific baselining/training process 500 returns to identifying 502 the next motion primitive to be recorded. The previously described aspects of the patient-specific baselining/training process 500 are then repeated until all motion primitives have been recorded and stored 510.

While the above patient-specific baselining/training process 500 has been described in terms of a single motion primitive and motion object and modifier (e.g., sitting down, stepping with a left leg, stepping with a right leg), it will be appreciated that baseline data can be recorded and stored 508 for a sequence of motion sentences. For example, baseline data is recorded for the sequence of sitting up in bed, followed by moving legs over the side of the bed, then standing, and then taking a step. In another example, baseline data is recorded for the sequence of walking to a door of the patient room, opening a door to the room, and walking out of the room. In still another example, a sequence of motion primitives motion sentences and sequence of motion sentences is recorded while the patient performs a six-minute test. Other sequences will be appreciated in light of the description herein.

FIG. 6 is a flow diagram illustrating one possible monitoring process 600 for measuring motion sensor output and classifying the motion or orientation as corresponding to a motion primitive, a motion sentence or a sequence of motion sentences.

The monitoring process 600 may be performed by a medical device including the medical device controller 300 or another programmable device including a motion recognition or classification component 316. In some implementations, the monitoring process 600 may be configured to occur on an external programmable device, e.g., a phone, personal digital assistant, tablet, or other electronic device that is separate from the medical device, but may also be carried by the patient wearing the medical device. In some instances, rather than being carried by the patient, such an external device may also be carried by a caregiver, a patient surrogate (e.g., a loved one), or other individual who may accompany the patient as the patient moves about. In one scenario, a nurse in a hospital environment may carry such a device while assisting the patient who may be moving within the hospital building. For example, such a phone, personal digital assistant, tablet, or other electronic device may be operably connected (e.g., via a wired or wireless connection) to the medical device and exchange information regarding the monitoring process 600 with the medical device.

In some implementations, the monitoring process 600 may be configured to occur at a remote server (e.g., at a medical device facility or a caregiver facility). For example, such a remote server may be in wireless connection with the medical device (e.g., via a BlueTooth® enabled base station, or a WiFi connection) and exchange information regarding the monitoring process 600 with the medical device.

The motion recognition or classification component 316 may be operating in a monitoring mode. The monitoring process 600 begins by acquiring and/or measuring 602 sensor data descriptive of the patient 102 in motion or at rest using the medical device. The sensor data is communicated to the medical device (or analogous device that is part of a distributed computing network) and recorded in a data store 330 (e.g., in the sensor data structure 400). Motion classification or recognition 604 is then performed (e.g., by the motion recognition or classification component 316) on the sensor data using any of a variety of machine learning techniques including an artificial neural network, Deep Learning Network, HMM, feature vector analysis and distance function analysis, cross correlation, threshold analysis, or other known techniques as discussed in detail above. If a statistical or probabilistic approach is taken to the motion classification or recognition process 604, a confidence level of the classification is determined as part of the operation of the machine learning or other classification technique. If the determined confidence level 608 is less than a threshold value that sets a minimum level of fit required to find a match, then the sensor data corresponding to the detected motion is flagged 606 for review by a caregiver. The monitoring process 600 ends after the flagging 606 of the sensor data.

If the determined confidence level 608 is greater than the confidence threshold, in the case of statistical recognition approaches, then the classified 604 motion sentence feature is added 610 to a current motion sentence (e.g., stored in the motion primitive data structure 406). In template matching approaches to motion recognition, motion sentences and sequences of motion sentences acquired during the baselining/training process may be stored as patient-specific baseline data (e.g., as stored in the motion sequence master 408). Measured motion, detected motion sentence features and motion sentences may then be matched to the generic motion sequence master data as well as the patient-specific baseline data to find a best match to motion sequences 612. For illustration, if the classified 604 motion sentence features are the motion primitive "Sitting" and the motion modifier "Up", and the previous orientation (past history) was "Lying down", and before that "Sleeping", then based on both the generic motion database, the patient-specific baseline data and the generic grammatical rules, the classification step 612 determines the full sentence is "Sitting up in bed". If the motion sequence is not recognized 614, the motion sequence is flagged 618 for review by a caregiver and the monitoring process 600 ends. However, if one or more defined motion sentences or motion sentence sequences are identified (i.e., not undefined 614), then the monitoring process 600 determines whether the sequence of motions by the patient is actionable (e.g., has data descriptive of an action stored in the motion sequence master 408 or is motion sentence or sequence of motion sentences that put the patient at incipient or immediate risk). If so, the monitoring process 600 executes a notification action (e.g., transmits a notification request to a notification component, e.g., the notification component 317). Examples of notification actions that may be requested for execution 620 via the notification component including warning a patient, a health care practitioner, or both of unauthorized, or high risk motions. If the sequence of motion primitives is not actionable, the monitoring process 600 executes the act 602. In act 616, the monitoring process determines whether the motion sequence is complete 616), for instance by using the stored grammatical rules. If the motion sequence is determined to be complete 616, then a new motion sequence is started (e.g., a new record is added to the motion sequences structure 410) and the monitoring process 600 executes the act 602.

Upon returning to the act 602, the monitoring process 600 continues by waiting for another patient motion to be detected via acquisition 602 of more sensor data. It is appreciated that, in some examples, the acts of flagging 606 and 618 described above may include issuing a urgent alert to a device associated with a caregiver to warn the caregiver than an unidentifiable motion has been performed by the patient 102.

In some examples, whether or not a motion sequence is actionable is at least partially based on contextual factors. For instance, in various examples of the act 616, the motion recognition or classification component 316 further evaluates the time of day, age of the patient, pre-existing medical conditions of the patient, whether a prescribed medical instruction regarding patient movements (e.g., uninterrupted bed rest, no more than 10 minutes of walking at a time) have been violated, and/or the operating mode of the motion recognition or classification component 316. In some examples, the motion recognition or classification component 316 is configurable between a daytime monitoring mode and nighttime monitoring mode. In these examples, some motion sequences may be actionable under the nighttime monitoring mode, but not actionable under the daytime monitoring mode, or vice versa. For instance, a motion sequence of a patient visiting the bathroom may not be actionable while the motion recognition or classification component 316 is operating in the daytime monitoring mode, but the same motion sequence may be actionable when the motion recognition or classification component 316 is operating in the nighttime monitoring mode. In some examples, the motion recognition or classification component 316 is configurable between a normal monitoring mode and a monitoring mode associated with a medical procedure, such as an intravenous fluid or medicine delivery, dialysis, or other medical procedure. For instance, a motion sequence of the patient standing may not be actionable while in normal monitoring mode, but the same motion sequence may be actionable when the patient is receiving dialysis or some other medical treatment (e.g., receiving sedatives) for which the patient has been prescribed bed rest.

Not all motion primitives need be recorded for every individual patient. For example, falling unsupported to the ground produces sensor data that is, for the most part, (a) distinctive among other motions primitive and (b) common to most patients. For this reason, pre-existing generic data that may be in the form of models, heuristic rules generated from a database of multiple patients and motions, or learned classification from prior collected data input to a HMM, deep learning network can, in some cases, be used for recognition of some motion sentence features, motion sentences, or motion sentence sequences. For instance, as a consequence of the distinctiveness and commonality of sensor data descriptive of patient falls, the classification process used can be more computationally specialized and efficient.

Figure 7:
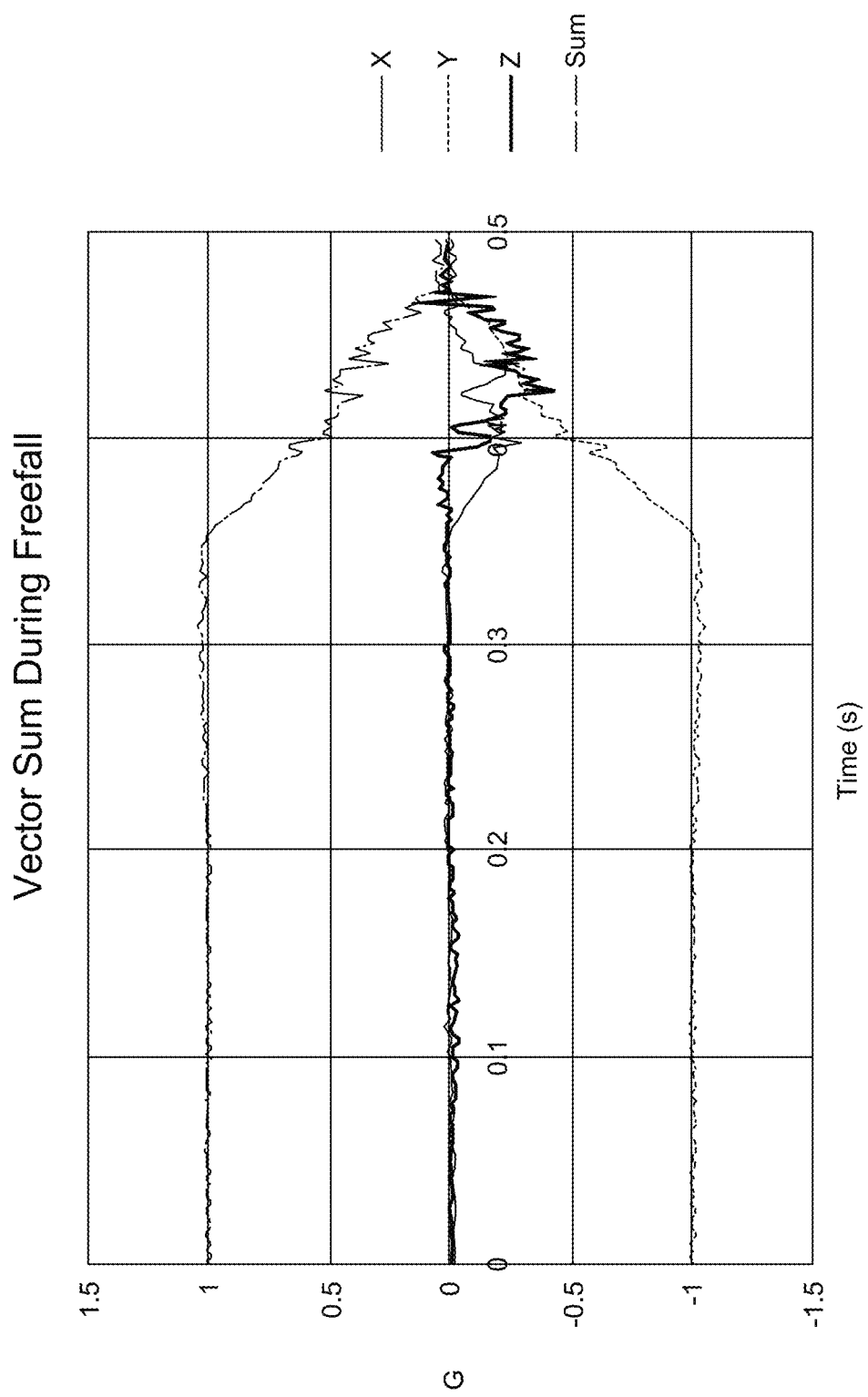
FIG. 7 is a graph of patient force vectors versus time during an unsupported fall of the patient to the ground.

FIG. 7 is an example of preexisting generic data that can be used to identify a sequence of motion primitives exhibited by a patient without requiring the patient himself to perform the motion primitive during the baselining/training process. FIG. 7 is a graph of forces that acted on a patient as a function of time during an unsupported fall to the ground. The forces shown are oriented in x, y, and z directions in a Cartesian coordinate system. A sum of the absolute value of these forces is also shown. While the example data shown in FIG. 7 was collected from a three-dimensional accelerometer, it is appreciated that alternative representations of the physical phenomena of an unsupported fall of a patient to the ground are possible depending on the sensor(s) used and the orientation of the sensors. The positive and negative sign of the data depicted in FIG. 7 was a function of the orientation of the three-dimensional accelerometer. For the purposes of explanation, only the magnitude as a function of time will be discussed.

As shown, at Time (t)=0 seconds (s), a patient was standing upright. Resisting the force of gravity, the patient (or more specifically the accelerometer attached to the patient) experienced a vertical force equal to 1 G (in the negative y direction according to the orientation of the accelerometer on the patient). This force of 1 G continued until approximately t=0.35 s, at which point the patient began an unsupported fall to the ground (also known as "free fall"). During freefall from t=0.35 s to approximately t=0.48 s, the net force acting on the patient declined because the patient was no longer resisting the pull of gravity by standing upright. This decline continued until the patient made contact with the ground. The various forces acting on the patient become approximately zero just before the patient impacted the ground.

Figure 8:
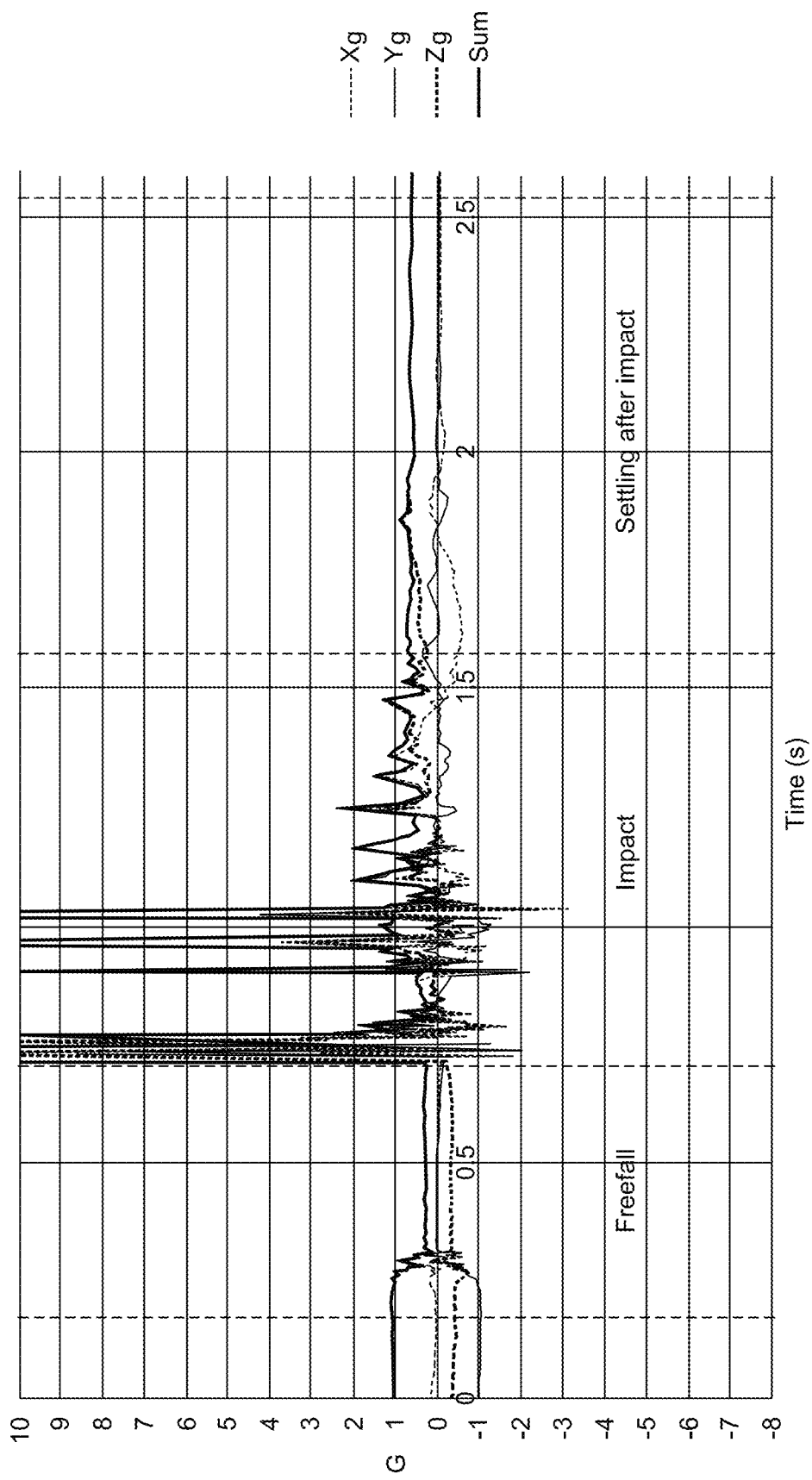
FIG. 8 is a graph of patient motion vectors versus time during an unsupported fall of the patient to the ground and after patient impact with the ground.

FIG. 8 displays data similar to the data shown in FIG. 7 but over a longer timescale. FIG. 8 further illustrates the forces experienced by the patient during and after impact with the ground. As in FIG. 8, a patient started out in a stable state with a net force acting on the patient of approximately 1 G. As the patient freefell toward the ground, the forces declined for the same reasons explained above. However, as indicated in the region labeled "Impact," once the patient made contact with the ground, the forces of impact were over 10 G. In the example shown, there were successive waves of high force as the patient bounces on the ground and as the forces of impact reverberated throughout the body of the patient. The impact forces eventually dissipated, as is shown in the region labeled "Settling after impact."

As with other motion primitives and sequences thereof, the classification of the motion primitives and motion sequences can be accomplished by comparing sensor data to various thresholds. Should the motion sequence be classified using this threshold comparison technique, the medical device controller 300 may trigger a notification, a warning, or an alarm (to the patient, a monitoring system, and/or a caregiver) via a notification component (e.g., the notification component 317) in response to the data crossing one or more of the thresholds. In the case of freefall, a sequence of motion primitives corresponding to the forces is stored as preexisting generic data and threshold forces are configured so as to detect a patient in freefall. These thresholds can include successively larger or smaller force values. As each threshold is exceeded, a new warning or alarm is initiated by the motion classification component via execution of the notification component. Examples of thresholds for falling can include 0.8 $G_0$, 0.5 $G_0$, and any values between to indicate progression of the patient toward the ground. In other examples, the thresholds that indicate settling after impact can be anywhere between 0.95 $G_0$ and 1.05 $G_0$. Also, as described above, a confidence metric can be determined from the motion or orientation sensor data and used as an additional threshold to engage a notification component. In examples, a mobile ambulatory device, such as example medical device 200, can also include systems that request a patient to confirm a fall, can notify bystanders (e.g., through an alarm) and/or, can notify health care providers that the patient has fallen.

Figure 9:
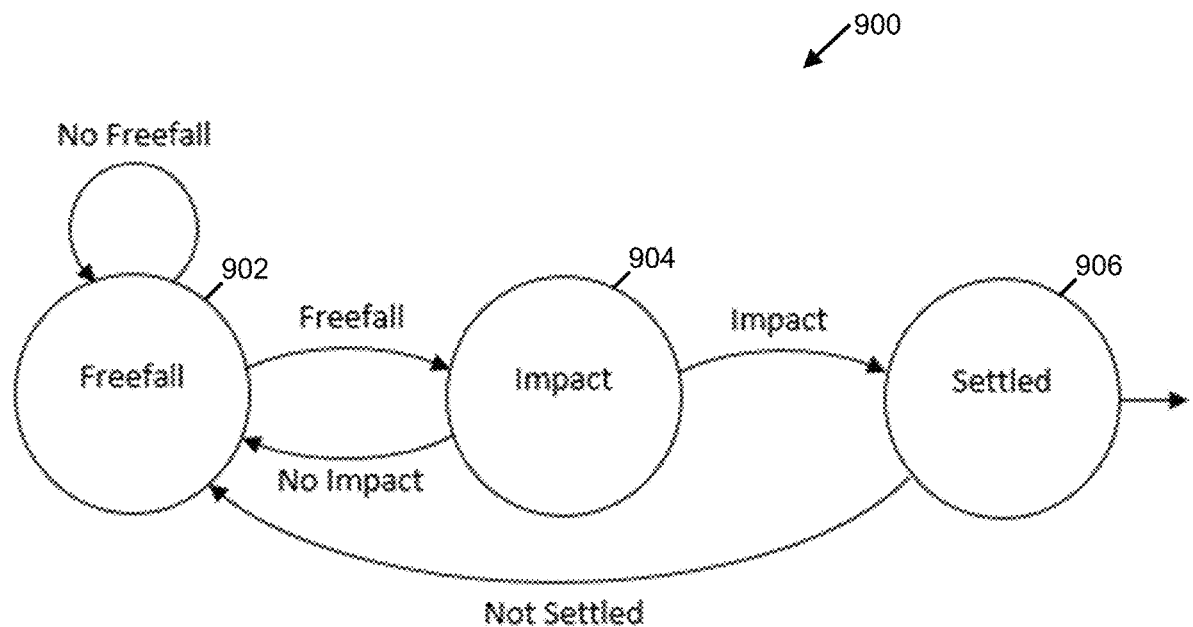
FIG. 9 is a schematic illustration of stages of patient motion during and after an unsupported fall of the patient to the ground.

FIG. 9 is a schematic illustration of a motion sequence 900 indicative of a patient fall. As shown, the first motion primitive of the sequence 900 includes a freefall motion primitive 902, an impact motion primitive 904, and a settled motion primitive 906. Within the context of the monitoring process 600, each of these motion primitives may be classified using a threshold comparison technique in the act 604, obviating a need for patient-specific baseline data. Further, the monitoring process 600 may determine that any motion sequence including a freefall motion primitive is actionable in the act 616 and, in response, take action in the act 620. This action may include executing a notification component configured to alert or warn the patient and/or a caregiver of the fall. In addition, the monitoring process 600 may take additional actions as the motion primitives 904 and 906 are added to the motion sequence.

In some examples, the motion primitives used to determine whether a patient has fallen may include data descriptive of orientation. For example, where patient's orientation changes abruptly from substantially vertical to substantially horizontal over a short period of time, some examples disclosed herein may identify this sequence of patient motion as a fall and take action accordingly.

Similar to the example of a patient falling presented above, preexisting generic motion sentence features, motion sentences, and sequences of motion sentences can be applied to the patient from simulated data or data generated by another patient or patients and may include disoriented movement, stumbling, and swooning. Analogously, the preexisting generic motion sentence features, etc. can be simulated or generated for shivering, coughing, and having a seizure, as shown in FIGS. 10, 11, and 12, and explained below in more detail.

Figure 10:
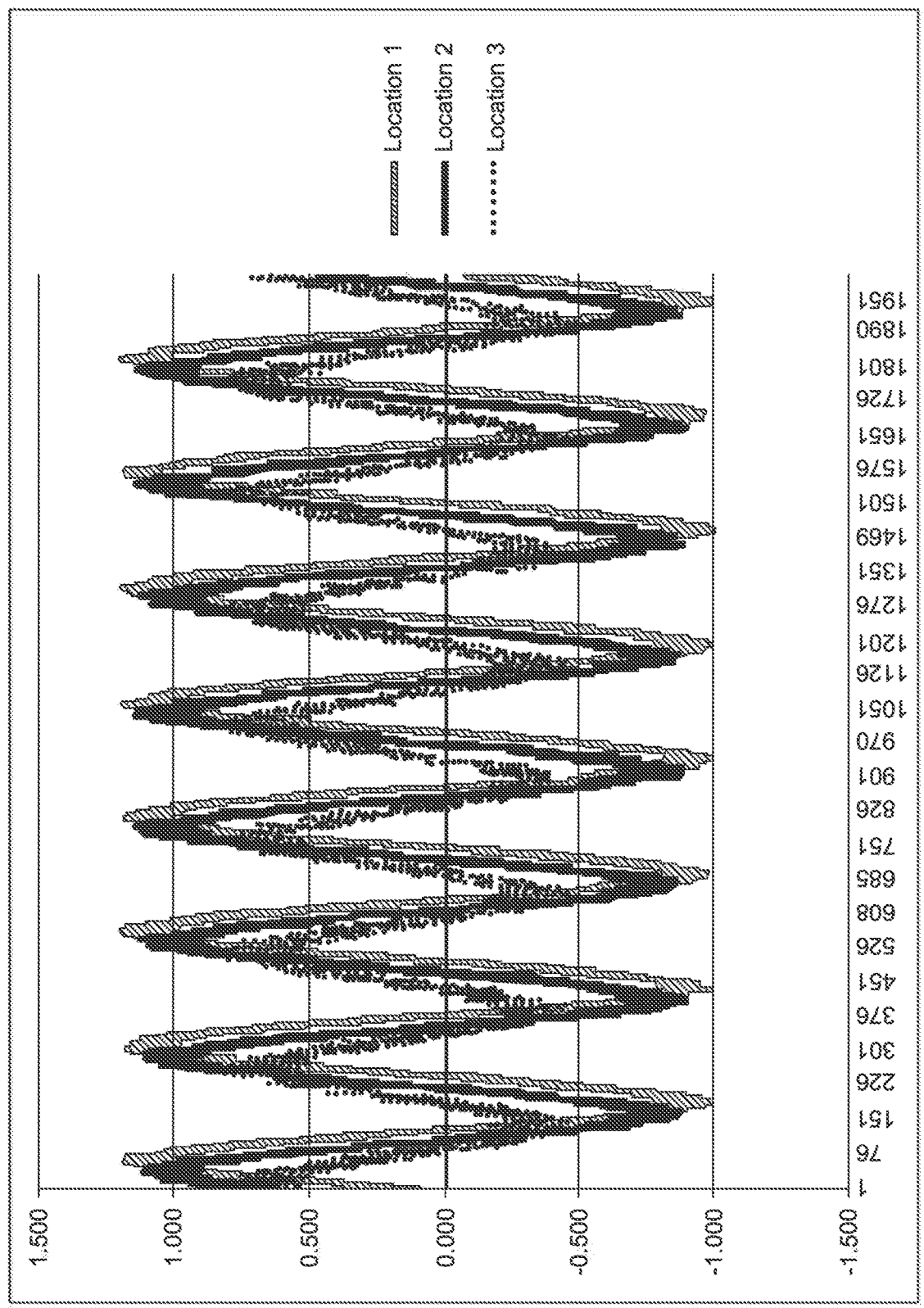
FIG. 10 is a graph illustrating vector sums of patient motion during an episode of patient shivering.

FIG. 10 is a graph of vector sums of patient motion acquired by three different motion/orientation sensors disposed at three different locations on the patient during an episode of patient shivering. In the example shown, shivering is detected as a high frequency (e.g., from approximately 50 Hz to approximately 100 Hz, or from approximately 100 Hz to approximately 1000 Hz) vibration. The main frequency may shift over time but not over a short period of time. In some examples, the high frequency vibration is detected in some or all of the axes in which a motion or orientation sensor is configured to detect motion (e.g., for a one-axis, two-axis, or three-axis accelerometer) and is located so that it can detect motion (e.g., the motion or orientation sensor movement is not restricted by being confined between a patient and a bed). In some examples, even though the net force on a patient will be approximately zero, the magnitude at different locations or in different axes may vary.

Figure 11:
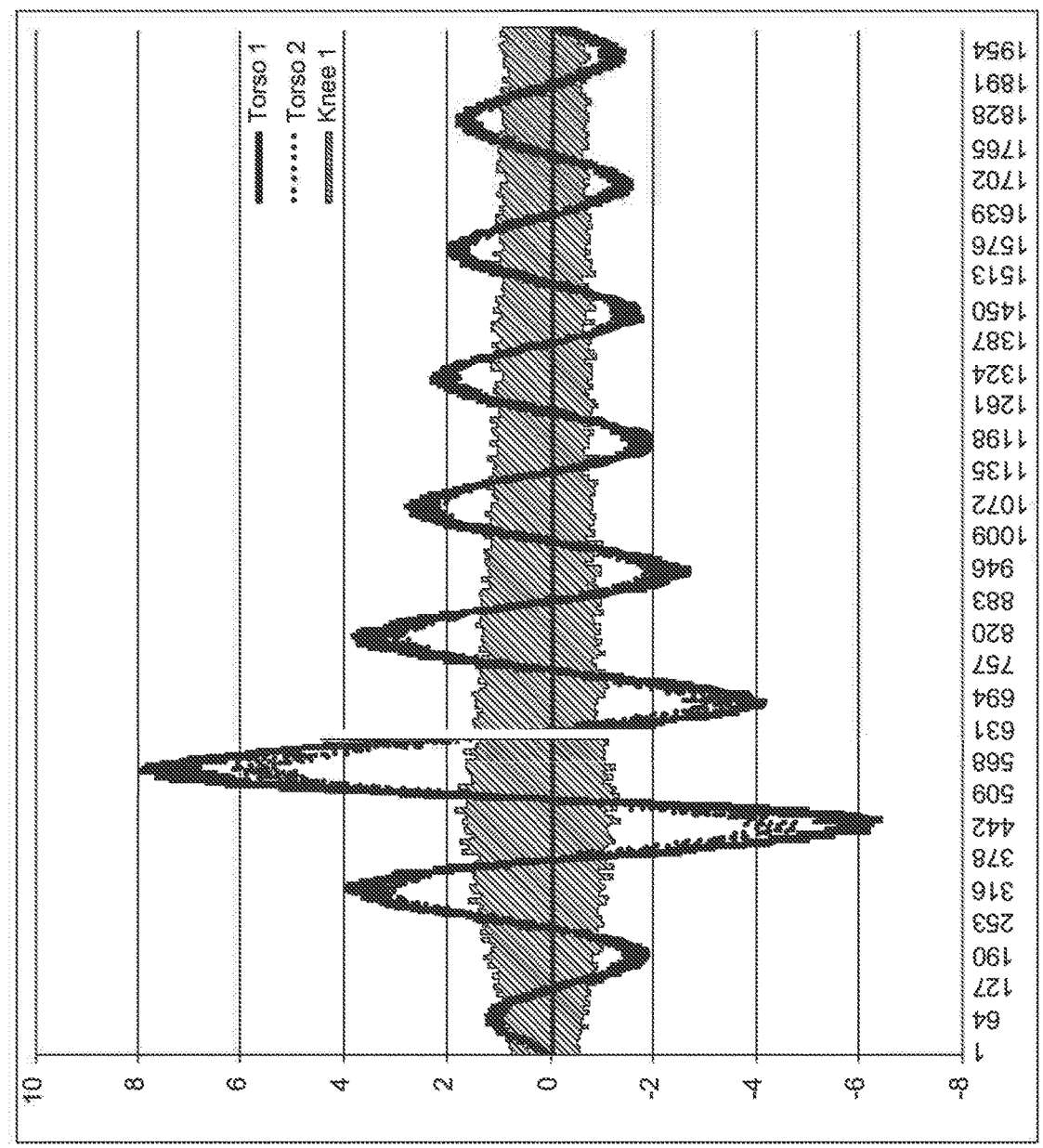
FIG. 11 is a graph illustrating vector sums of patient motion during an episode of patient coughing.

FIG. 11 is a graph of vector sums of patient motion acquired by three different motion/orientation sensors disposed at three different locations (two locations on a torso and one location on a knee) on the patient during an episode of patient coughing. As shown, a pattern of forces from coughing can be depicted as a high force acceleration in some directions. These high force accelerations are transient. That is, as a function of time, the forces detected by the motion or orientation sensor(s) on a patient torso last on the order of a few seconds. Because each cough is accompanied by a compression of a patient's diaphragm, motion sensors disposed on a torso proximate to the diaphragm are more likely to detect the forces caused by coughing.

Figure 12:
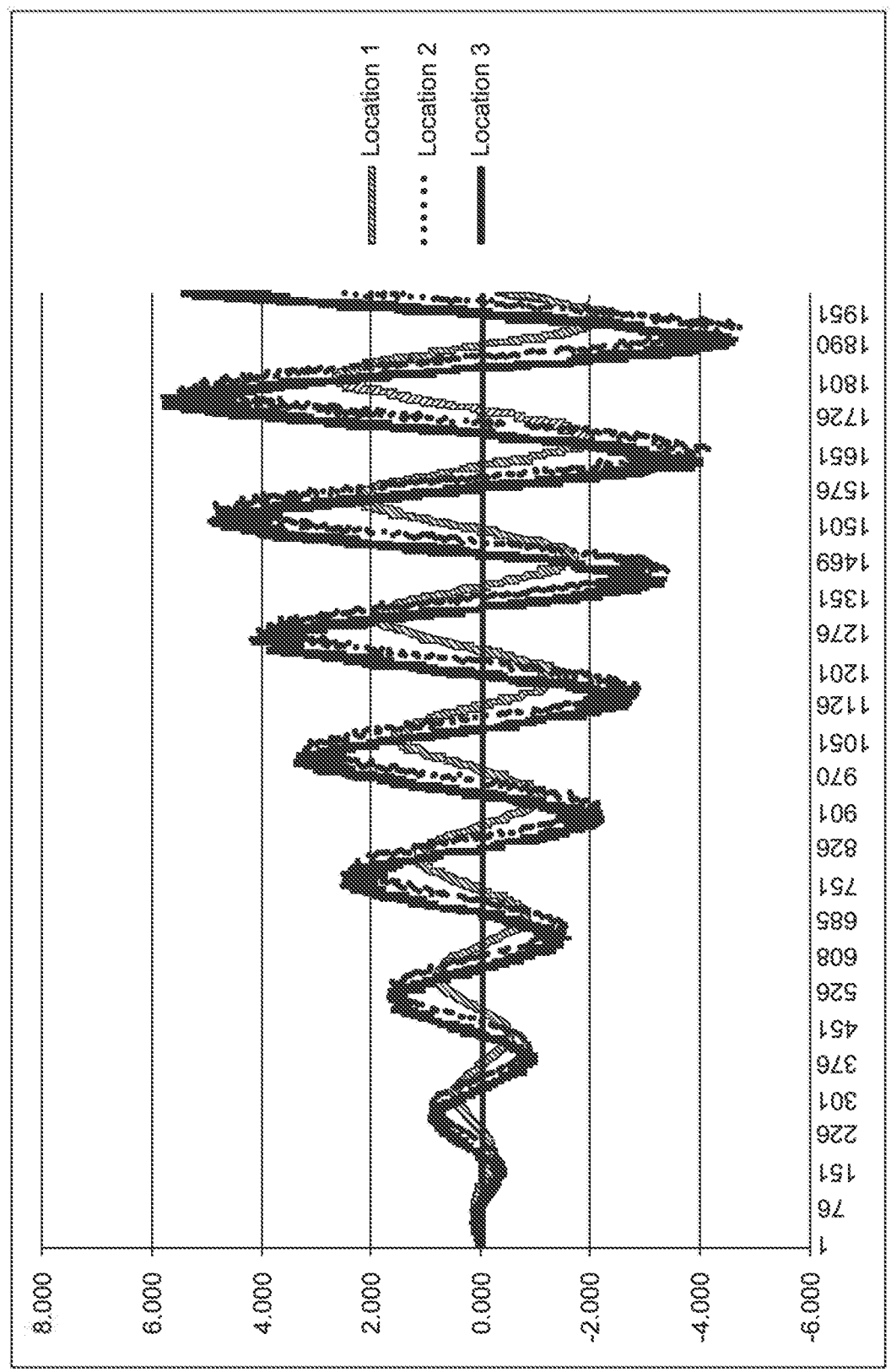
FIG. 12 is a graph illustrating of vector sums of patient motion during an episode of patient seizure.

FIG. 12 is a graph of vector sums of patient motion acquired by three different motion/orientation sensors disposed at three different locations on the patient during an episode of patient seizure. In the example showing the vector sums of a seizure illustrated in FIG. 12, a cyclic variation in forces is detected by the motion/orientation sensors. Unlike the cyclic frequency detected from coughing (illustrated in FIG. 11), the cyclic frequency of the example seizure shown in FIG. 12 increases in amplitude as a function of time and occurs over a longer time scale than coughing. Motion due to various types of seizure may vary between patients and between causes of seizures. For example, motion primitives detected during a febrile seizure may be different from those detected during a grand mal seizure. It will be appreciated that different types of seizures may employ different preexisting generic data—it is unlikely to be able to get patient-specific baseline data for many of these types of situations.

Regardless of whether shivering, coughing, seizing, stumbling, or disoriented movement is analyzed, in some examples it useful to analyze vector sums from each motion or orientation sensor so that the net force as a function of time is identified for each motion or orientation sensor. In some cases, a reference motion or orientation sensor that is stationary (e.g., attached to a proximate stationary surface, such as a bed, or relatively stationary surface, such as gurney or ambulance) can be used to further identify patient movement that occurs in place (e.g., shivering while lying in bed) or during ambulatory patient movement. Alternatively or concurrently, non-summed force vectors can be analyzed to determine whether patient movement is asymmetric (e.g., a seizure only on a left side or lack of movement on a left side of the patient).

The processes disclosed herein each depict one particular sequence of acts in a particular example. The acts included in these processes may be performed by, or using, one or more programmable devices specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Example Hospital Environment

Figure 13:
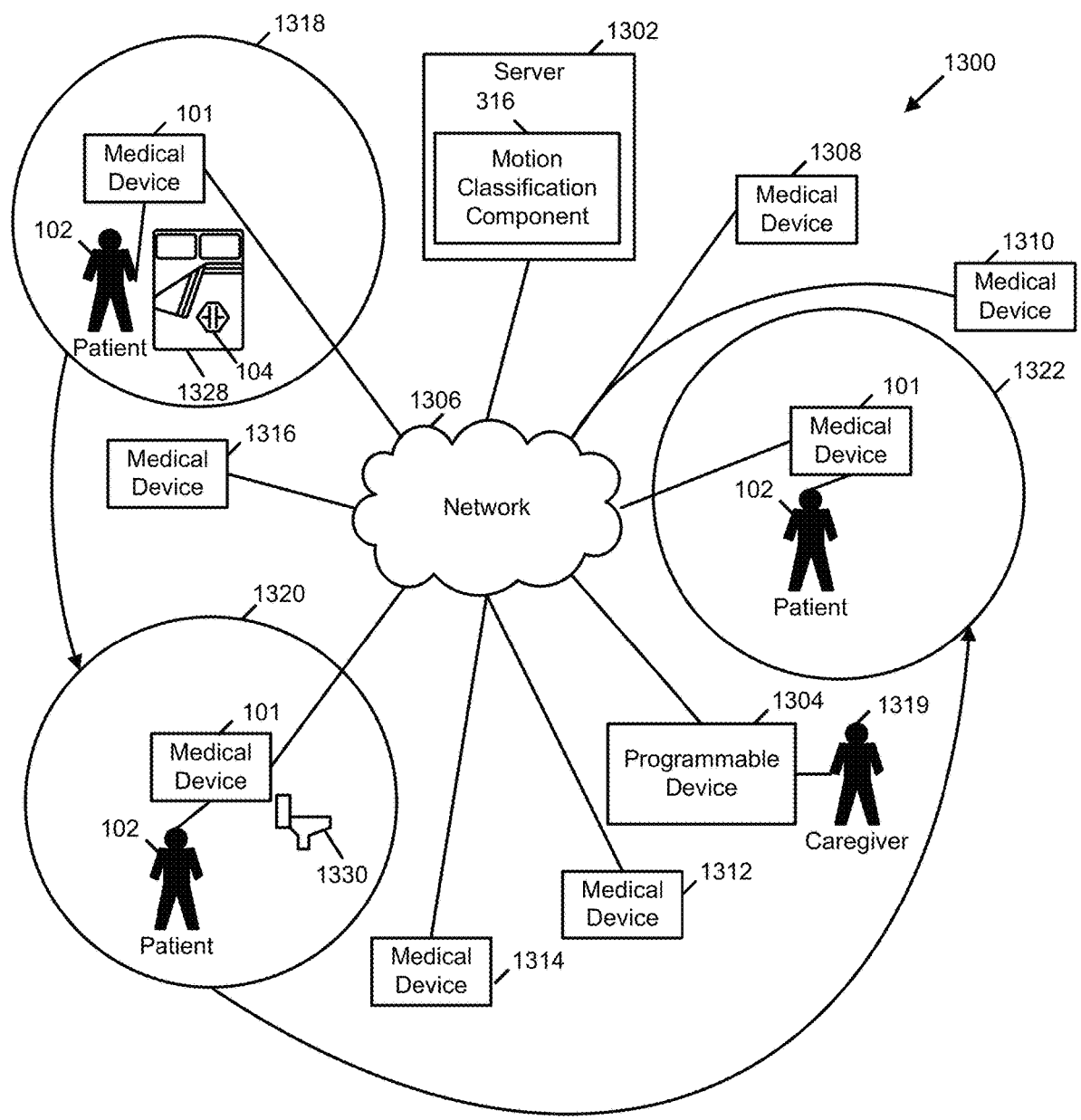
FIG. 13 is a schematic diagram of one example of a distributed computer system within a hospital environment in accordance with an example of the present disclosure.

FIG. 13 is a schematic diagram of one example 1300 of a distributed computer system within a hospital environment in accordance with an example of the present disclosure. The example 1300 includes programmable devices 1302 and 1304, a network 1306, and various medical devices 101, 1308, 1310, 1312, 1314, and 1316. For example, the programmable devices in the network 1306 include a remote server 1302 and one or more client devices 1304 such as secured and authorized personal digital assistants or Internet-enabled smartphones used by a caregiver or other authorized personnel to access the network 1306 as described in further detail below. In one example in accordance with FIG. 13, the medical device 101 is associated with the patient 102 and includes at least one of the sensor arrangement 100 and the ambulatory medical device 200. The example 1300 illustrates various locations within the hospital environment 1318, 1320, and 1322 to which the patient 102 and the medical device 101 travel over time.

The server 1302 includes any computing device that includes one or more processors and is configured for communication with one or more remote computing devices through the network 1306. The server 1302 also includes the motion recognition or classification component 316 described above. In some examples, the server 1302 maintains a local motion information data store that includes motion information stored in the motion information data store 330.

The client device 1304 can include various computing devices that can be placed in communication with the network 1306. In some examples, the client device 1304 is a computing device capable of receiving user input as well as transmitting and/or receiving data via the network 1306. For example, the client device 1304 can be carried by the patient. For example, the client device 1304 can be carried by a caregiver, such as a nurse or a physician. In one embodiment, the client device 1304 is a conventional computer system, such as a desktop or laptop computer. In another embodiment, the client device 1304 is a device having computer functionality, such as a personal digital assistant (PDA), mobile telephone, tablet computer, smartphone or similar device. In one example, the client device 1304 executes an application allowing a user (e.g., the caregiver 1319) to interact with the network 1306 and receive data and analyses of motion primitives and/or motion sequences of various patients, thus becoming a specialized computing machine. In at least one example, the client device 1304 is located at the caregiver's station and includes a notification component 317 configured to receive notification requests from a motion classification component (e.g., the motion recognition or classification component 316). The client device 1304 can, in response to receiving the requests, perform one or more client device actions including, e.g., present one or more notifications to a caregiver or a patient.

In some implementations, the remote server 1302 may be configured to store the output of the motion recognition or classification process in one or more databases. In such cases, the data can be grouped by type of motion data, date and time of day that the data was collected, and/or annotation of the data based on analysis of the information. An authorized person such as a caregiver or support personnel may cause the server 1302 (e.g., via client device 1304) to generate one or more reports based on the data. For example, such reports may be ordered by the type of data, and date and time of day the data was collected.

The network 1306 may comprise any combination of local area and/or wide area networks, using both wired and wireless communication systems. In one embodiment, the network 1306 uses standard communications technologies and/or protocols. Thus, the network 1306 may include links using technologies such as Ethernet, IEEE 802.11, worldwide interoperability for microwave access (WiMAX), 3G, 4G, CDMA, digital subscriber line (DSL), etc. Similarly, the networking protocols used on the network 1306 may include multiprotocol label switching (MPLS), transmission control protocol/Internet protocol (TCP/IP), User Datagram Protocol (UDP), hypertext transport protocol (HTTP), simple mail transfer protocol (SMTP) and file transfer protocol (FTP). Data exchanged over the network 1306 may be represented using technologies and/or formats including hypertext markup language (HTML) or extensible markup language (XML). In addition, all or some of links can be encrypted using conventional encryption technologies such as secure sockets layer (SSL), transport layer security (TLS), and Internet Protocol security (IPsec).

In some examples, the medical devices 1308, 1310, 1312, 1314, and 1316 can be any medical device or an assembly of medical devices that can communicate with the network 1306 and with other devices capable of communicating with and through the network 1306. Examples include a cardiac defibrillator, a "crash cart" on which are stored a cardiac defibrillator and various other devices, drugs, and tools used to resuscitate a patient experiencing cardiac arrest, a wheelchair, a gurney or mobile hospital bed, among others. These devices, and others not explicitly mentioned here, may be configured to communicate with the network 1306 and the motion recognition or classification component 316 in the server 1302 as described below.

In a first example location 1318, the patient 102 wearing a medical device 101 gets out of a hospital bed 1328 that is equipped with its own motion/orientation sensor 104. As described above, the relative movement between the medical device 101 worn by the patient 102 and the motion/orientation sensor 104 attached to the stationary hospital bed 1328 is detected. The detected motion data is transmitted through the network 1306 to the server 1302 and classified by the motion recognition or classification component 316 using methods and systems described above. In one example, the motion/orientation sensors of the medical device 101 can transmit data to the motion recognition or classification component 316 that is used to determine a number of steps taken by the patient using a sequence of motion primitives (e.g., patient-specific baseline data recorded during a six-minute walk test). A distance between the patient 102 and the hospital bed 1328 is estimated using the determined number of steps. Based on this estimate, and any thresholds previously set regarding one or more permitted distances between the patient 102 and the hospital bed 1328, an action can be executed such as notifying hospital personnel of the patient movement. Similarly, bystanders may also be notified so that they can help the patient 102 return to bed. In some examples, the motion/orientation sensor 104 attached to the hospital bed is in communication with one or more processors directly coupled to the motion/orientation sensor 104 (or similar inertial measurement unit (IMU) of the hospital bed 1328. Any of the processors and/or motion/orientation sensors may also include a network interface. This configuration can improve the response time and computational efficiency when using the motion/orientation sensor 104 of the hospital bed 1328 to monitor patient movements.

Examples of patient movements that can be monitored include walking, as presented above, but also more subtle patient movements in which having a stationary reference point, such as the motion/orientation sensor 104 attached to the hospital bed 1328, can be helpful. These patient movements include shivering, coughing, having a seizure, stumbling, swooning or other disoriented movement. While having a stationary reference point is one example that can be used to detect these movements, it is not required. It will be appreciated that other examples may rely on baseline data recorded, measured, and analyzed during a baselining or training period that has the patient engage in various activities such as walking, sitting in bed, normal breathing, sleeping and other similar activities to more accurately detect and classify patient motion as shivering, coughing, having a seizure, stumbling, swooning or other disoriented movement. In some cases the preexisting, generic data used for these are generated from models or are generic data (such as that in the examples of FIGS. 7 and 8), and not specific to the patient 102. In still other examples the processor associated with the motion/orientation sensor 104 of the hospital bed or the processor associated with the server 1302 classifies the patient movement at least in part by comparing a magnitude of the patient movement to a first threshold and a frequency of the patient movement to a second threshold.

In other examples, depending on the classifying motion of the patient, the motion recognition or classification component 316 is configured to identify a medical device associated with a condition of the patient and proximal to the patient, such as medical device 1316, and to instruct the medical device to issue an alert via the notification component 317. For example, if the classified motion is that of the patient 102 getting out of bed and then having cardiac arrest (as detected by the medical device 101), then the motion recognition or classification component 316 will, in response to the classified motion and cardiac arrest detection, identify a crash cart proximate to the patient, such as medical device 1316. If so equipped, the medical device 1316 can issue an alert (such as a tone, a flashing light, or an electronic notification identifying its coordinates in the hospital to client device 1304 associated with caregiver 1319) so that the medical device 1316 is located by a responding caregiver. Systems and methods for determining the location of a medical device near a patient are described in International Patent Application No. PCT/US15/66720, titled SYSTEMS AND METHODS OF DETERMINING LOCATIONS OF MEDICAL DEVICES RELATIVE TO WEARABLE DEVICES, filed Dec. 18, 2015, and published as WO/2016/106132, which is hereby incorporated herein by reference in its entirety.

In example location 1320, the motion sequence of the patient 102 is classified as walking to toilet 1330. In example location 1322, the motion sequence of the patient 102 is classified as walking out of the door of his assigned hospital room. As described above, the medical device 101 is worn by the patient 102. The motion/orientation sensors of the medical device 101 record motion data, transmit the data through the network 1306 to the remote server 1302, where motion recognition or classification component 316 classifies it using various Motion Recognition algorithms previously discussed. Alerts, warnings, or other actions are taken depending on thresholds associated with the motions of the patient 102, as described above.

In still another example, the examples described above can be used in a hospital or clinical environment to track a location of a patient 102 within the hospital or clinic in combination with some, all, or none of the embodiments described above. That is, in addition to monitoring patient movements and orientation, some examples include using proximity sensors, beacons, and infrastructure for various area networks (e.g., Wi-Fi or ZigBee network) to identify a location (or approximate location depending on the measurement discrimination of the technology employed). Analogous to some of the examples described above, various thresholds regarding patient location can be established so that the patient and/or a care giver is notified upon the patient exceeding a threshold. Additional details for examples that include tracking patient location are described in U.S. Patent Application Publication 2016/0278652.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. An ambulatory medical device for monitoring movement of a patient, comprising:
   a plurality of motion sensors configured to be located at one or more anatomical locations on a patient's body and to detect a plurality of motion parameters corresponding to a motion of a portion of the patient's body;
   a plurality of electrocardiogram (ECG) electrodes configured to be disposed on the patient's body and to acquire ECG signals descriptive of cardiac activity of the patient; and
   at least one processor communicatively coupled to the plurality of motion sensors and the plurality of ECG electrodes, the at least one processor configured to
      prompt, via a user interface, the patient to perform a motion primitive during an initial period of use of the ambulatory medical device, wherein prompting the patient to perform the motion primitive includes prompting the patient to walk;
      receive, from a particular one of the motion sensors, a patient-specific baseline motion parameter value that characterizes patient motion when the patient performs the motion primitive;
      receive, from one or more of the motion sensors, patient-specific baseline walking parameter values that characterize a baseline number of steps taken by the patient;
      store, in a motion primitive master data structure, a record that associates the motion primitive with the patient-specific baseline motion parameter value generated by the particular one of the motion sensors;
      train a motion recognition process using the patient-specific baseline motion parameter value;
      after the initial period of use, receive the plurality of motion parameters corresponding to the motion of the portion of the patient's body;
      store, in a data store, the plurality of motion parameters;
      process the plurality of motion parameters stored in the data store to determine the motion of the portion of the patient's body;
      use the motion recognition process, as trained using the patient-specific baseline motion parameter value, to classify the motion of the portion of the patient's body into a classification based on a plurality of predetermined motion sentence features that describe a sequence of movements that includes the motion primitive;
      use the patient-specific baseline walking parameter values and the plurality of motion parameters stored in the data store to determine an estimated distance that the patient has moved;
      initiate one or more notification actions based on one or more of the estimated distance or the classification;
      identify, using the ECG signals, a cardiac arrhythmia experienced by the patient;
      determine, at least partially based on the identified cardiac arrhythmia, a treatment protocol to be administered to the patient;
      modify the identified treatment protocol based on the motion of the portion of the patient's body, thus resulting in a modified treatment protocol; and
      cause delivery of a therapeutic shock to the patient in accordance with the modified treatment protocol,
      wherein modifying the identified treatment protocol includes delaying application of the therapeutic shock to the patient when the motion of the portion of the patient's body transgresses a predetermined threshold amount of movement or a predetermined duration of movement.

2. The ambulatory medical device of claim 1, wherein the plurality of motion parameters comprises at least one orientation parameter corresponding to an orientation of the portion of the patient's body.

3. The ambulatory medical device of claim 1, wherein the plurality of motion sensors comprises at least one of an accelerometer, a gyroscope, or a magnetometer.

4. The ambulatory medical device of claim 1, wherein the plurality of predetermined motion sentence features further comprises at least one predetermined motion object.

5. The ambulatory medical device of claim 1, wherein the motion of the portion of the patient's body is classified using first sensor data acquired from a first motion sensor of the plurality of motion sensors attached to a first location and second sensor data acquired from a second motion sensor attached to a second location.

6. The ambulatory medical device of claim 5, wherein the first location is an anatomical location of the one or more anatomical locations on the patient's body and the second location is a location of a physical object other than the patient's body.

7. The ambulatory medical device of claim 6, wherein the physical object comprises at least one of a bed or a wheelchair.

8. The ambulatory medical device of claim 1, wherein the one or more anatomical locations on the patient's body comprises one or more of a head, chest, leg, neck, shoulder, elbow, knee, wrist, jaw, forearm, bicep, ankle, or foot of the patient's body.

9. The ambulatory medical device of claim 1, wherein the patient-specific baseline walking parameter values are recorded during a six-minute walk test period.

10. The ambulatory medical device of claim 1, wherein the one or more notification actions comprises notifying a caregiver about the motion of the portion of the patient's body.

11. The ambulatory medical device of claim 1, wherein the one or more notification actions comprises warning the patient based on the motion of the portion of the patient's body.

12. The ambulatory medical device of claim 1, wherein the at least one processor is configured to identify another medical device separate from the ambulatory medical device proximal to the patient and to instruct the identified another medical device to issue an alert.

13. The ambulatory medical device of claim 1, wherein the at least one processor is configured to identify a current time and to execute an action associated with the current time.

14. The ambulatory medical device of claim 1, wherein the at least one processor is configured to classify the motion of the portion of the patient's body as at least one of disoriented movement, falling, stumbling, swooning, seizure, shivering, or coughing.

15. The ambulatory medical device of claim 1, wherein the ambulatory medical device comprises a wearable defibrillator.

16. The ambulatory medical device of claim 1, wherein the ambulatory medical device comprises a mobile cardiac monitoring device.

17. The ambulatory medical device of claim 1, wherein the one or more notification actions presents the estimated distance as an observed number of steps taken by the patient.

18. The ambulatory medical device of claim 1, wherein the one or more notification actions are initiated in response to the estimated distance exceeding a predetermined permitted distance.

19. A system for monitoring movement of a patient, the system comprising:
an ambulatory medical device comprising
a plurality of motion sensors configured to be located at one or more anatomical locations on a patient's body to detect a plurality of motion parameters corresponding to a motion of a portion of the patient's body;
a plurality of electrocardiogram (ECG) electrodes configured to be disposed on the patient's body and to acquire ECG signals descriptive of cardiac activity of the patient; and
at least one processor communicatively coupled to the plurality of motion sensors and the plurality of ECG electrodes, the at least one processor configured to
prompt, via a user interface, the patient to perform a motion primitive during an initial period of use of the ambulatory medical device, wherein prompting the patient to perform the motion primitive includes prompting the patient to walk;
transmit, to a remote server, a patient-specific baseline motion parameter value that is received from a particular one of the motion sensors, and that characterizes patient motion when the patient performs the motion primitive;
transmit, to the remote server, patient-specific baseline walking parameter values that are received from one or more of the motion sensors, and that characterize a first number of steps taken by the patient;
transmit, to the remote server, the plurality of motion parameters corresponding to the motion of the portion of the patient's body;
identify, using the ECG signals, a cardiac arrhythmia experienced by the patient;
determine, at least partially based on the identified cardiac arrhythmia, a treatment protocol to be administered to the patient;
modify the determined treatment protocol based on the motion of the portion of the patient's body, thus resulting in a modified treatment protocol; and
cause delivery of a therapeutic shock to the patient in accordance with the modified treatment protocol, wherein modifying the determined treatment protocol includes delaying application of the therapeutic shock to the patient when the motion of the portion of the patient's body transgresses a predetermined threshold amount of movement or a predetermined duration of movement; and
the remote server configured to
receive the patient-specific baseline motion parameter value and the patient-specific baseline walking parameter values;
store, in a motion primitive master data structure, a record that associates the motion primitive with the patient-specific baseline motion parameter value generated by the particular one of the motion sensors;
train a motion recognition process using the patient-specific baseline motion parameter value;
after the initial period of use, receive the plurality of motion parameters corresponding to the motion of the portion of the patient's body;
store, in a data store, the plurality of motion parameters;

process the plurality of motion parameters stored in the data store to determine the motion of the portion of the patient's body;

use the motion recognition process, as trained using the patient-specific baseline motion parameter value, to classify the motion of the portion of the patient's body into a classification based on a plurality of predetermined motion sentence features that describe a sequence of movements that includes the motion primitive;

use the patient-specific baseline walking parameter values and the plurality of motion parameters stored in the data store to determine an estimated distance that the patient has moved; and initiate one or more notification actions based on one or more of the estimated distance or the classification.

20. The system for monitoring patient movement of claim 19, further comprising: at least one client device in communication with the remote server, the at least one client device configured to notify at least one of a caregiver or the patient about the motion of the portion of the patient's body based on the one or more notification actions.

21. The ambulatory medical device of claim 19, wherein the one or more notification actions comprise warning the patient based on the motion of the portion of the patient's body.

* * * * *